(12) United States Patent
Norris et al.

(10) Patent No.: US 11,130,937 B2
(45) Date of Patent: Sep. 28, 2021

(54) COMPOSITIONS AND METHODS FOR LONG-TERM IN VITRO CULTURE OF THE SYPHILIS SPIROCHETE

(71) Applicant: THE BOARD OF REGENTS OF THE UNIVERSITY OF TEXAS SYSTEM, Austin, TX (US)

(72) Inventors: Steven J. Norris, Houston, TX (US); Diane G. Edmondson, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/422,155

(22) Filed: May 24, 2019

(65) Prior Publication Data

US 2020/0032201 A1  Jan. 30, 2020

Related U.S. Application Data

(60) Provisional application No. 62/676,024, filed on May 24, 2018.

(51) Int. Cl.
| | | |
|---|---|---|
| *C12N 1/18* | (2006.01) | |
| *C12N 1/20* | (2006.01) | |
| *G01N 33/50* | (2006.01) | |
| *C12N 5/00* | (2006.01) | |
| *C12N 5/07* | (2010.01) | |

(52) U.S. Cl.
CPC ............ *C12N 1/20* (2013.01); *C12N 1/18* (2013.01); *C12N 5/0018* (2013.01); *C12N 5/06* (2013.01); *G01N 33/5008* (2013.01); *C12N 2502/09* (2013.01)

(58) Field of Classification Search
None
See application file for complete search history.

(56) References Cited

U.S. PATENT DOCUMENTS

2016/0177260 A1* 6/2016 Shoji .................. A61P 25/14
424/93.21

OTHER PUBLICATIONS

Uzarski et al (Biomaterials. Jun. 2017. 129: 163-175).*
Rampersad, S. (Sensors (Basel). 2012. 12(9): 12347-12360).*
Mapes et al (Physiol Genomics Apr. 2014. 46(8): 302-308).*
Cox, David L. "Culture of Treponema pallidum." *Methods in Enzymology*. vol. 236. Academic Press, 1994. 390-405.
Edmondson et al., "Long-Term In Vitro Culture of the Syphilis Spirochete *Treponema pallidum* subsp. Pallidum", *MBio* 9.3 (2018).
Norris et al., "Biology of Treponema pallidum: correlation of functional activities with genome sequence data." *J Mol Microbiol Biotechnol.* 3:37-62, 2001.

* cited by examiner

*Primary Examiner* — Jennifer E Graser
(74) *Attorney, Agent, or Firm* — Parker Highlander PLLC

(57) ABSTRACT

Presented herein are compositions and methods for the long-term in vitro culturing of *Treponema* species such as *T. pallidum*. Culture media and systems for *Treponema* culture are also provided.

19 Claims, 13 Drawing Sheets

Specification includes a Sequence Listing.

FIGS. 1A-C

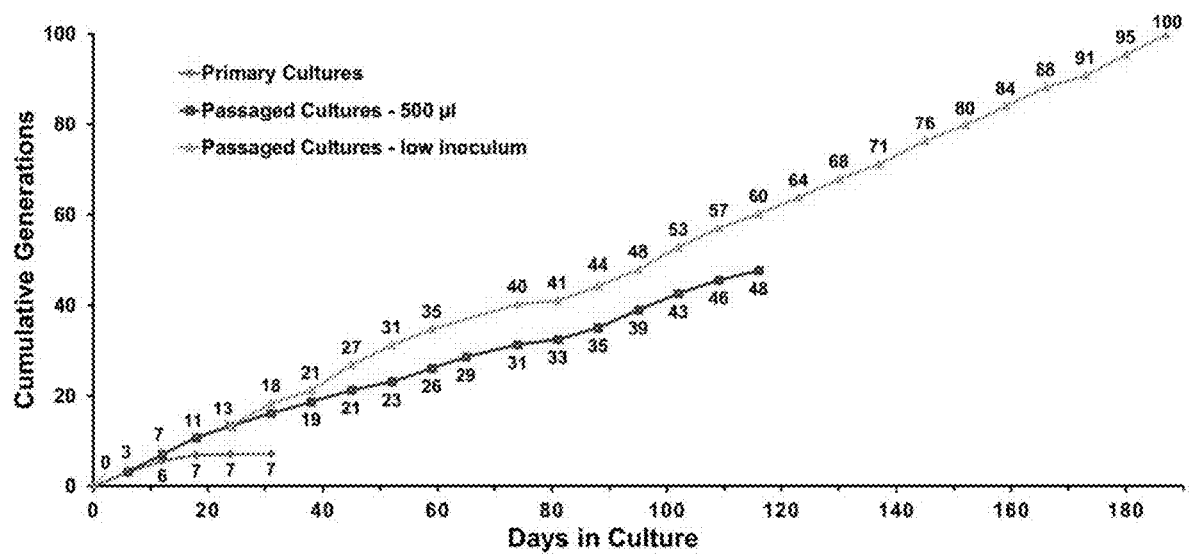
FIG. 2
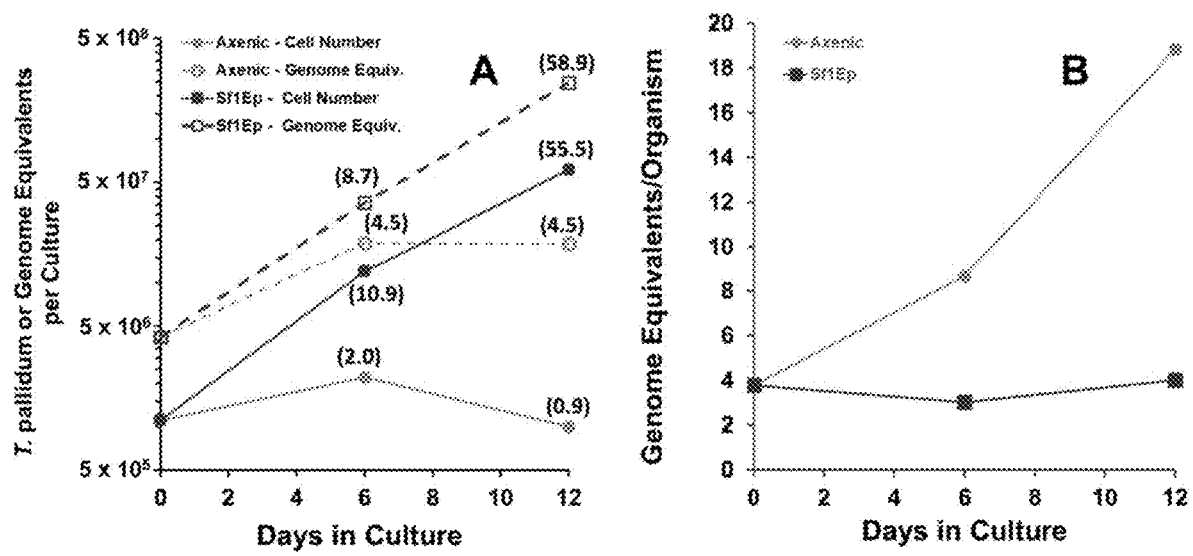
FIGS. 3A-B

FIGS. 6A-C

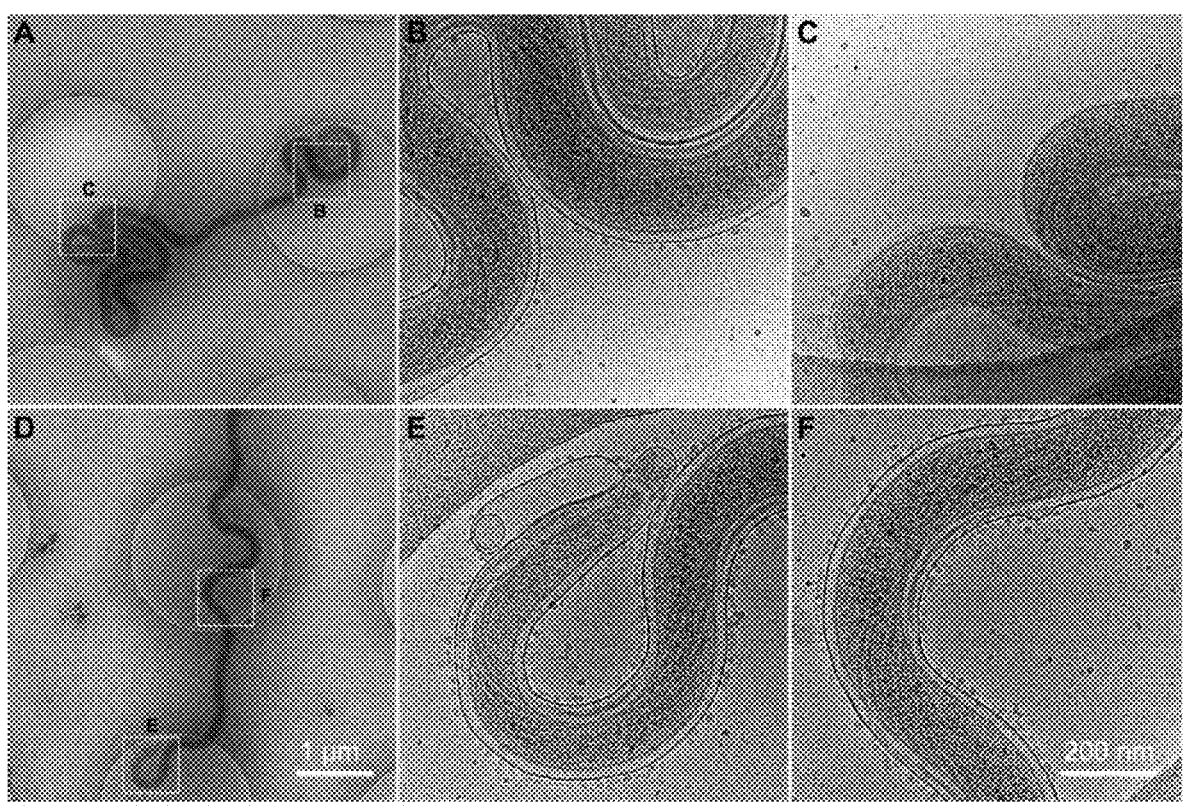
FIGS. 7A-F

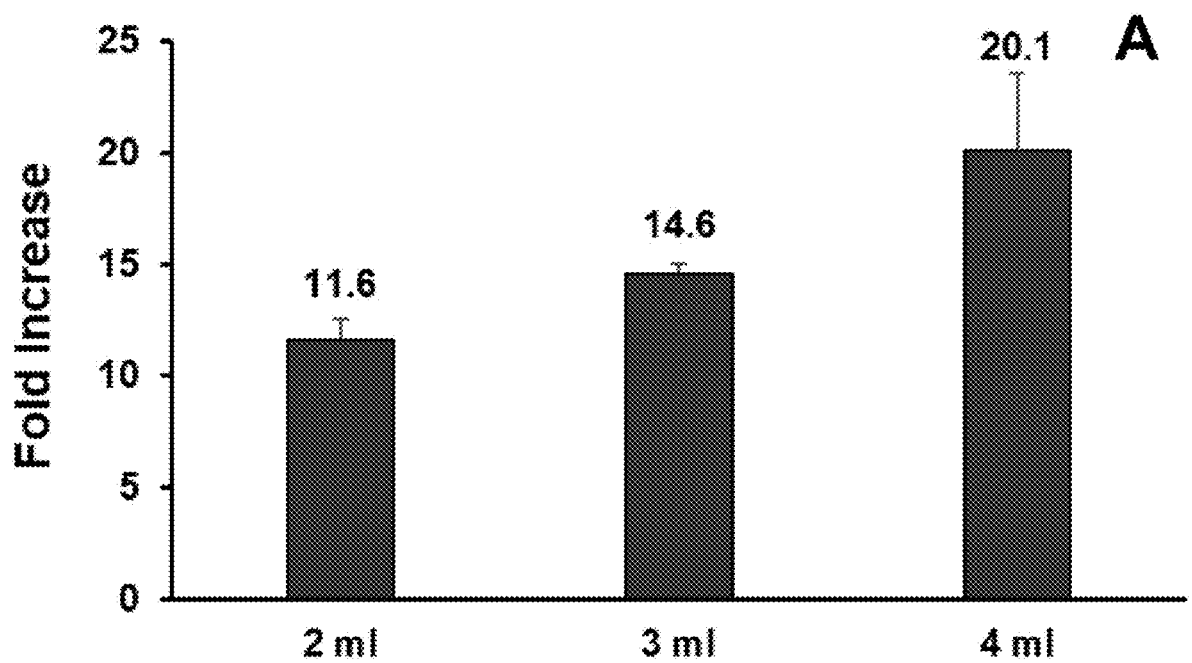
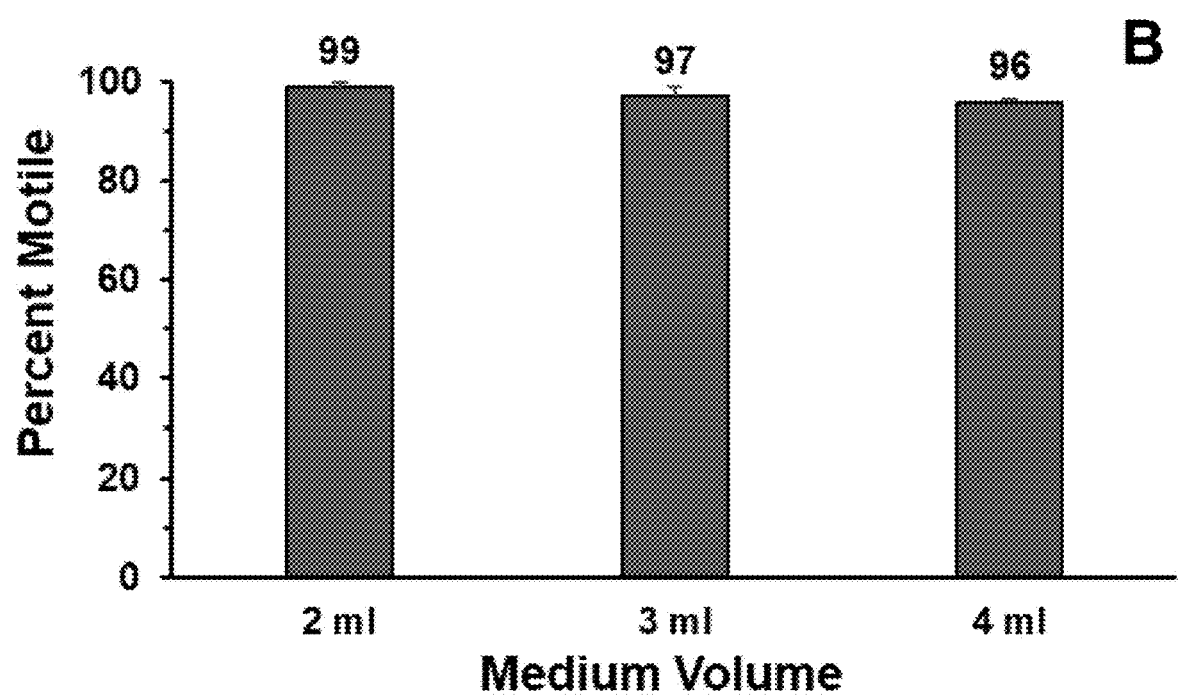
FIGS. 8A-B

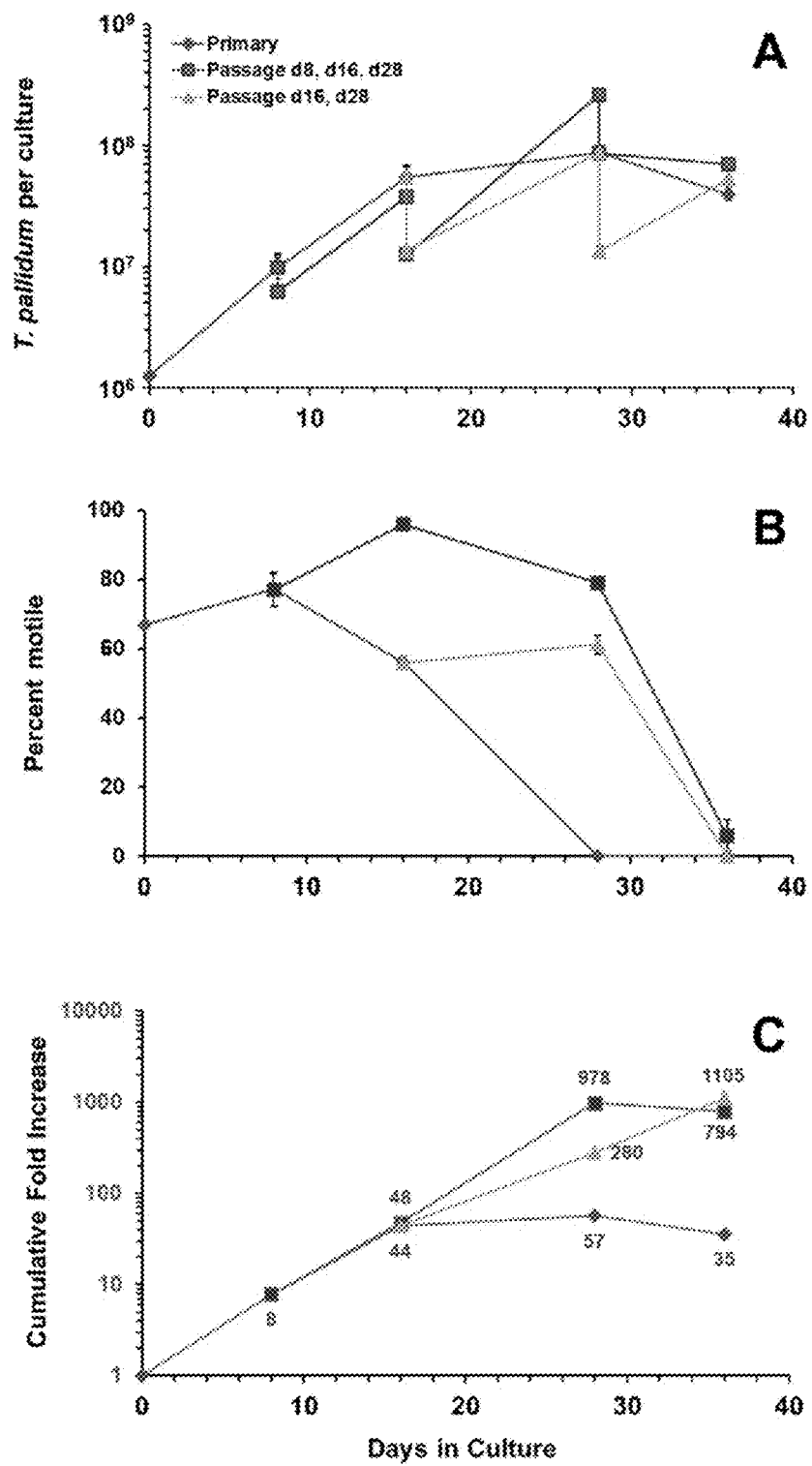
FIGS. 9A-C

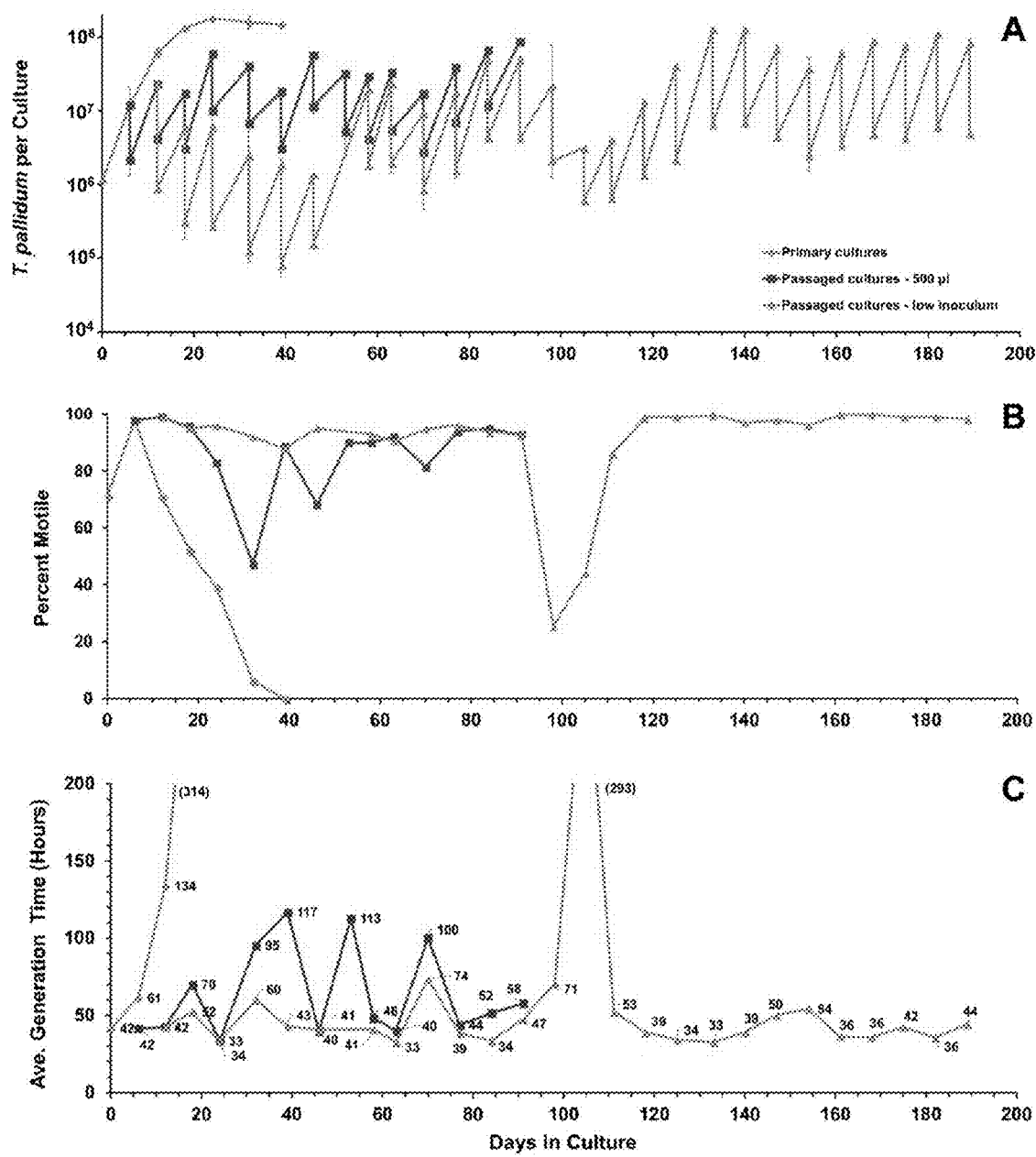
FIGS. 10A-C

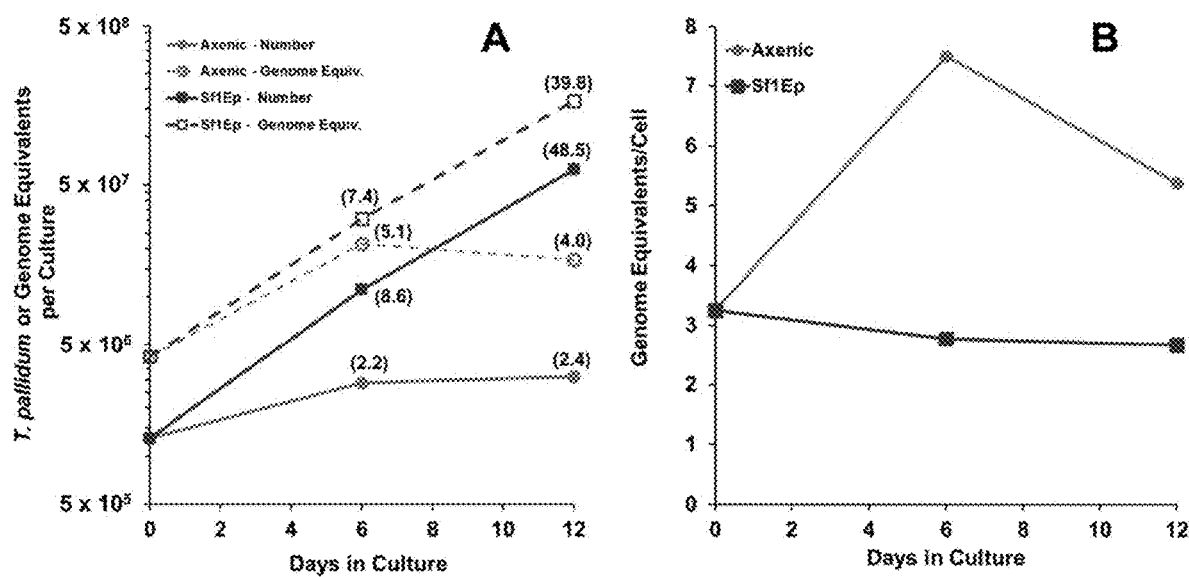
FIGS. 11A-B

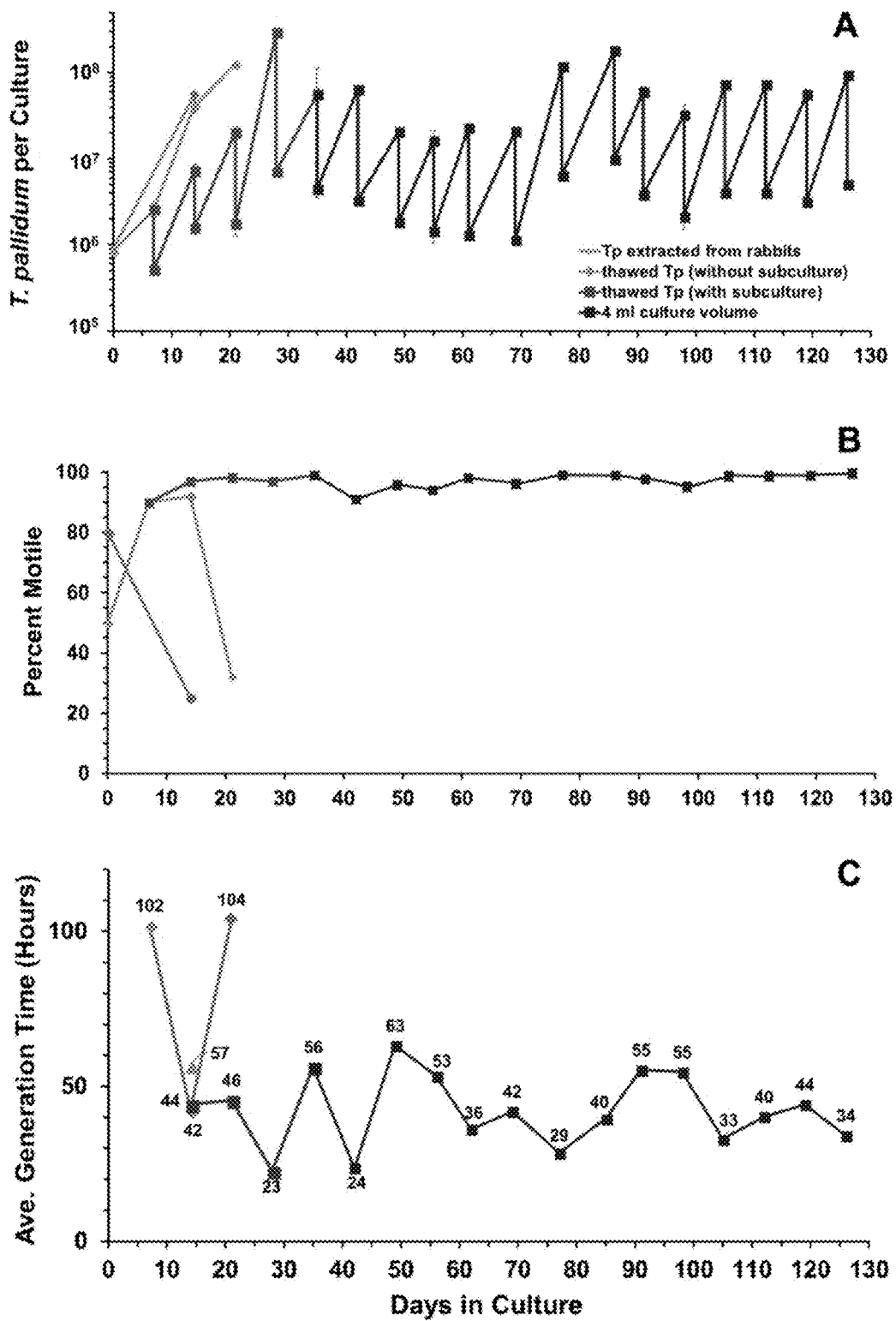
FIGS. 12A-C

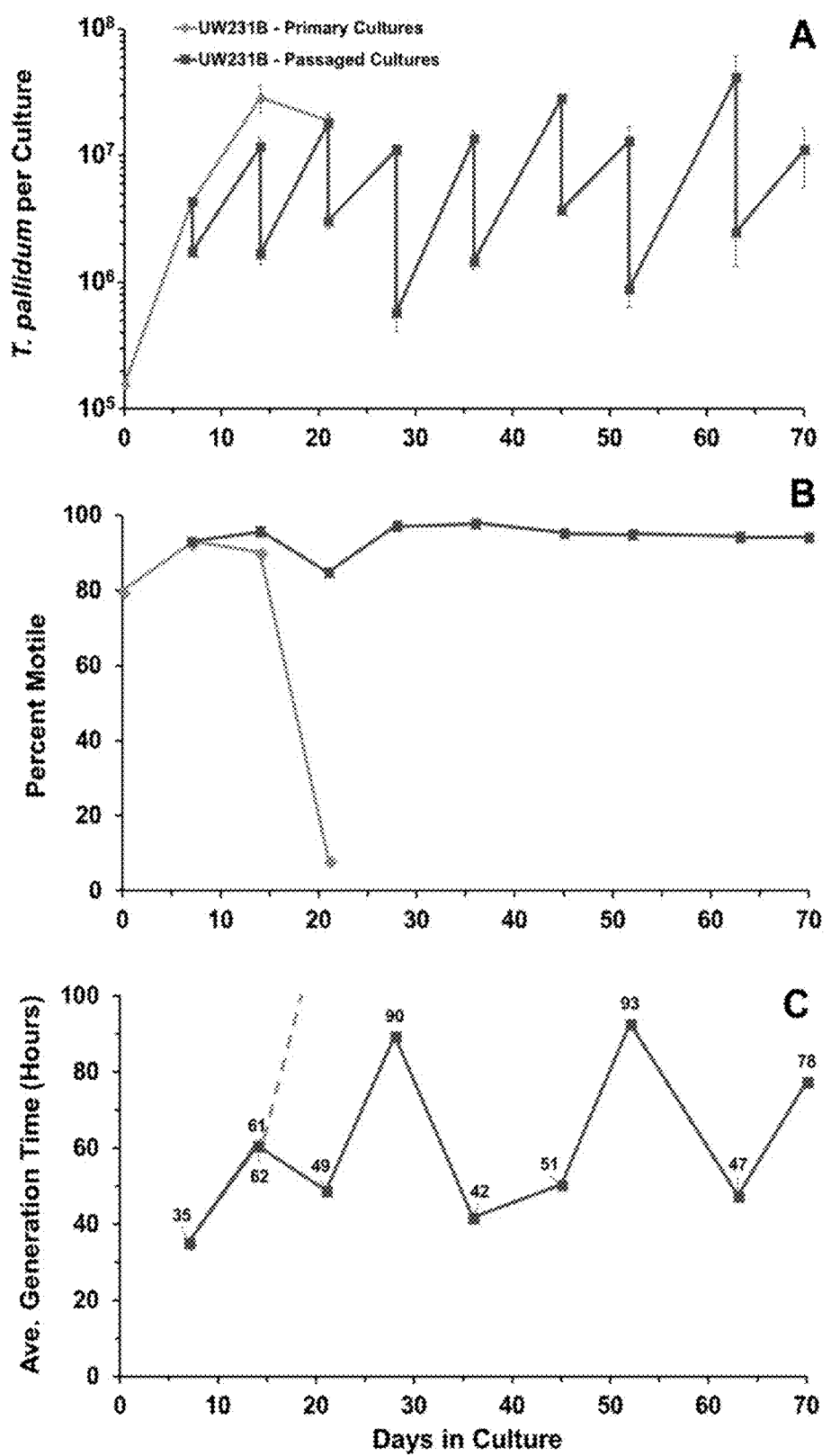
FIGS. 13A-C

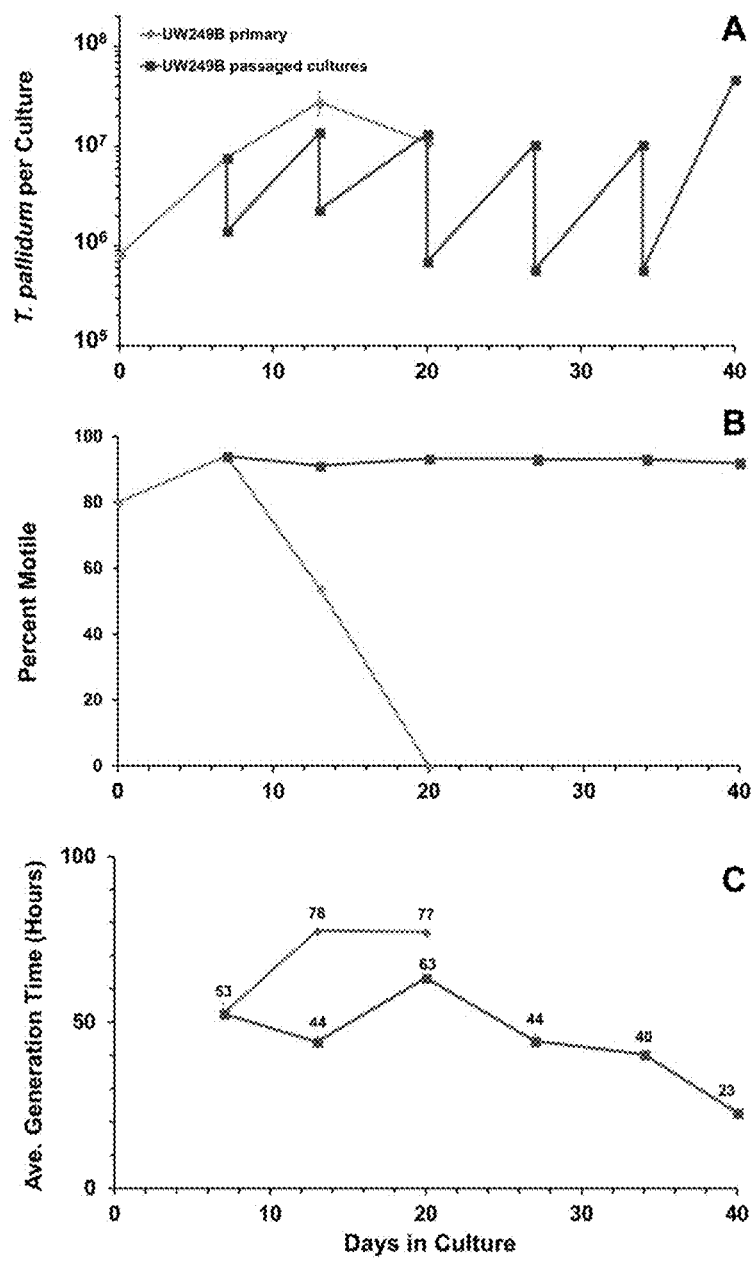
FIGS. 14A-C

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial sequence
<220> FEATURE:
<223> OTHER INFORMATION: Synthetic primer

<400> SEQUENCE: 1
caggatccgg catatgtcc                                                  19

<210> SEQ ID NO 2
<211> LENGTH: 23
<212> TYPE: DNA
<213> ORGANISM: Artificial sequence
<220> FEATURE:
<223> OTHER INFORMATION: Synthetic primer

<400> SEQUENCE: 2
aagtgtgagc gtctcatcat tcc                                             23
```

COMPOSITIONS AND METHODS FOR LONG-TERM IN VITRO CULTURE OF THE SYPHILIS SPIROCHETE

This application claims the benefit of U.S. Provisional Patent Application No. 62/676,024, filed May 24, 2018, the entirety of which is incorporated herein by reference.

The invention was made with government support under Grant No. R21AI128494, awarded by the National Institutes of Health. The government has certain rights in the invention.

BACKGROUND OF THE INVENTION

1. Field of the Invention

The present invention relates generally to the field of microbiology. More particularly, it concerns compositions and methods for culturing *Treponema pallidum*.

2. Description of Related Art

Syphilis is a multistage sexually transmitted infection of world-wide importance, with an estimated 5.6 million new cases per year (World Health Organization 2016). *Treponema pallidum* subsp. *pallidum* (*T. pallidum*), the causative agent of syphilis, was first identified by Schaudinn and Hoffman in 1905 (Schaudinn and Hoffmann, 1905a; Schaudinn and Hoffmann, 1905b) as 'very light, thin spiraled microorganisms, turning around their largest length and moving back and forth.' Rapid progress in the study of this bacterium was made within five years, with the verification of the presence of spirochetes in experimentally infected animals by Metchnikoff and Roux (Metchnikoff and Roux, 1906), the invention of darkfield microscopy for easy visualization of *T. pallidum* by Karl Landsteiner, development of the first serologic test for syphilis by von Wassermann et al. (von Wassermann et al., 1906), and the introduction of arsphenamine by Paul Ehrlich as an effective, relatively nontoxic anti-syphilis agent (Gensini et al., 2007; Ehrlich, 1909). Successful culture of *T. pallidum* was reported almost immediately and during the subsequent decades (Schereschewsky, 1909; Kast and Kolmerk, 1929), but these reports were found to be either irreproducible or the result of contamination with nonpathogenic *Treponema* species that colonize human skin (Noguchi, 1916). During the 1970s, progress was made in characterizing some *T. pallidum* physiologic properties, most notably its microaerophilic nature and improved survival in the presence of mammalian cells (Norris et al., 2001).

In 1981, Fieldsteel, Cox and Moeckli (Fieldsteel et al., 1981) reported the consistent occurrence of up to 100-fold multiplication of *T. pallidum* in a co-culture system consisting of Sf1Ep cottontail rabbit epithelial cells, a modified tissue culture medium with heat-inactivated fetal bovine serum, dithiothreitol (DTT) as a reducing agent, and a microaerobic atmosphere containing 1.5% $O_2$. These results were reproduced in hundreds of experiments (primarily by the Cox and Norris groups), and reported in over 25 publications (reviewed in (Norris et al., 2001; Cox, 1994). However, treponemal multiplication and survival were limited to 12 to 18 days, despite efforts to refine this system. Attempts to subculture *T. pallidum* provided little improvement in the cumulative fold increase or survival of the bacterium (Norris et al., 2001; Cox, 1994; Norris and Edmondson, 1987). The same limitation has existed for the closely related organisms that cause yaws (*T. pallidum* subsp. *pertenue*), bejel (*T. pallidum* subsp. *endemicum*), pinta (*Treponema carateum*), and venereal spirochetosis in rabbits and hares (*T. paraluiscuniculi*) (Norris et al., 2003; Giacani and Lukehart, 2014). The inability to culture these organisms continuously in vitro has necessitated their propagation in rabbits for use in research, greatly hindering investigation of these important pathogens.

SUMMARY OF THE INVENTION

In some embodiments, the present disclosure provides a culture system comprising a co-culture of a population of *Treponema* species organisms and a population of mammalian epithelial cells, wherein said co-culture is present in microaerobic conditions and in the presence of a medium comprising excess nutrients, and wherein the said *Treponema* species organisms are in direct contact with the mammalian epithelial cells. In some aspects, the mammalian epithelial cells are rabbit epithelial cells. In specific aspects, the cells are Sf1Ep cells. In certain aspects, the mammalian epithelial cells exhibit low nutrient requirements. In some aspects, the mammalian epithelial cells can be grown for at least 5 days in a medium without depleting the nutrients in the medium. In certain aspects, the mammalian epithelial cells can be grown for at least 6, 7, 8, 9, 10, 11, 12, 13, 14 or 15 days in a medium without depleting the nutrients in the medium. In some aspects, the system comprises at least about $10^5$, $10^6$, $10^7$ or $10^8$ mammalian cells.

In some aspects of the embodiments, the *Treponema* species organisms are present in the co-culture in a proportion of between about 1:1 and 10,000:1 relative to the mammalian epithelial cells. In some aspects, the *Treponema* species organisms are present in the co-culture in a proportion of between about 1:1 and 1,000:1; or 1:1 and 100:1; or 10:1 and 100:1 relative to the mammalian epithelial cells. In some aspects, the co-culture is an adherent cell culture. In certain aspects, the co-culture is in a well or plate. In specific aspects, the co-culture is not a suspension culture.

In aspects of the embodiments, the *Treponema* species comprises *T. pallidum*, *T carateum*, or *T. paraluiscuniculi*. In particular aspects, the *Treponema* species comprises *T. pallidum* subsp. *pallidum*, *T. pallidum* subsp. *pertenue* or *T. pallidum* subsp. *endemicum*. In specific aspects, the *Treponema* species comprise is *T. pallidum* subsp. *pallidum*. In certain aspects, the *Treponema* species comprise *T. pallidum*, subsp. *pallidum* Nichols (hereafter referred to as *T. pallidum* Nichols). In some aspects, at least 60% (e.g., 70%, 80%, 90%, 95%, or 100%) of the *Treponema* species are viable. In certain aspects, at least 60% (e.g., 70%, 80%, 90%, 95%, or 100%) of the *Treponema* species exhibit motility. In particular aspects, at least 60% (e.g., 70%, 80%, 90%, 95%, or 100%) of the *Treponema* species exhibit infectivity.

In some aspects of the embodiments, the medium is a CMRL 1066-based medium. In certain aspects, the medium comprises a reducing agent. In some aspects, the medium comprises one or more of the components of Table 1. In certain aspects, the medium comprises one or more of the components of Table 2. In some aspects, the concentration of the one or more components of Table 2 is present at a concentration 0.01-fold to 0.1-fold, 0.1-fold to 10-fold, or 10-fold to 100-fold of the concentration of said component in Table 2.

In some aspects, the co-culture is in an environment comprising oxygen, carbon dioxide, and nitrogen. In some aspects, the co-culture is in an environment comprising about 3% to 0.5% oxygen. In specific aspects, the co-culture is in an environment comprising about 1.5% $O_2$, 5% $CO_2$, and balanced with $N_2$. In some aspects, the medium comprises one or more of: nucleic acid bases, nucleosides, cocarboxylase, Coenzyme A, flavin adenine dinucleotide, NAD, NADP, sodium acetate, sodium glucouronate, the fatty acid mixture and/or Tween 80. In particular aspects, the pH of the system is between about 6.0 and 8.0, such as 6.5, 7.0, or 7.5. In specific aspects, the medium is a TpCM-2 medium.

In some embodiments, the present disclosure comprises a method for culturing cells of the genus *Treponema*, comprising maintaining a culture system according to any of the provided embodiments or aspects. In some embodiments, the culture is passaged or given medium supplementation between about every 2 to about every 14 days, such as every 3, 4, 5, 6, 7, 8, 9, 10, 11, 12, 13, or 14 days. In certain aspects, the culture is passaged or given medium supplementation between about every 3 to about every 10 days, such as every 4, 5, 6, 7, 8, or 9 days. In some aspects, the culture is passaged between about every 3 to about every 10 days, such as every 4, 5, 6, 7, 8, or 9 days. In specific aspects, the culture is passaged between about 6 to about every 7 days. In some aspects, passaging comprises treatment of the culture with trypsin and addition of fresh culture medium. In some aspects, the *Treponema* cells remain viable for at least about one month in culture. In certain aspects, the *Treponema* cells remain viable for at least about three months in culture. In specific aspects, the *Treponema* cells remain viable for at least about six months in culture.

In some embodiments, there is provided a method for identifying an anti-*Treponema* compound, comprising: (a) contacting a candidate compound with a culture system according to any of the present embodiments or aspects; and (b) identifying a compound that inhibits *Treponema* replication, motility and/or infectivity.

In another embodiment, the present disclosure provides a culture medium comprising CMRL 1066, sodium pyruvate, Resazurin, a buffering agent, fetal bovine serum, at least one amino acid, at least one sugar or sugar alcohol and at least one reducing agent. In some aspects, the culture medium further comprises $NaHCO_3$. In specific aspects, the CMRL 1066 does not comprise glutamine or phenol red prior to addition to the medium. In certain aspects, the CMRL 1066 is present at a final concentration of about 0.5 to about 1×. In specific aspects, the CMRL 1066 is present at a final concentration of about 0.8×. In particular aspects, the glutamine is in the L-glutamine form. In certain aspects, the sodium pyruvate is present at a concentration of between about 0.5 and about 5 mM. In specific aspects, the sodium pyruvate is present at a final concentration of about 0.73 mM. In some aspects, the Resazurin is present at a final concentration of about 0.0005% to about 0.005%. In specific aspects, the Resazurin present at a final concentration of about 0.001%. In some aspects, the buffering agent is MOPS. In specific aspects, the MOPS is present at a final concentration of between about 2 and about 200 mM. In certain aspects, the MOPS is present at a final concentration of about 20 mM. In specific aspects, the MOPS is at a pH of about 7.5. In some aspects, the $NaHCO_3$ is present at a final concentration of between about 15 and about 25 mM. In certain aspects, the $NaHCO_3$ is present at a final concentration of about 19.2 mM. In some aspects, the at least one sugar or sugar alcohol comprises glucose. In certain aspects, the glucose is in the D-glucose form. In particular aspects, the glucose is present at a final concentration of between about 5 and about 50 mM. In specific aspects, the glucose is present at a final concentration of about 17.6 mM. In some aspects, the at least one amino acid comprises glutamine. In certain aspects, the glutamine is present in the L-glutamine form. In particular aspects, the glutamine is present at a final concentration of between about 0.2 mM and about 20 mM. In specific aspects, the glutamine is present at a final concentration of about 2 mM. In some aspects, the at least one sugar or sugar alcohol comprises mannitol. In certain aspects, the mannitol is in the D-mannitol form. In particular aspects, the mannitol is present at a final concentration of between about 0.1 mM and about 10 mM. In specific aspects, the mannitol is present at a final concentration of about 0.88 mM. In some aspects, the at least one amino acid comprises histidine. In certain aspects, the histidine is in the L-histidine form. In particular aspects, the histidine is present at a final concentration of about 0.05 to 5 mM. In specific aspects, the histidine is present at a final concentration of about 0.52 mM. In some aspects, the reducing agent comprises dithiothreitol. In certain aspects, the dithiothreitol is in the DL-dithiothreitol form. In some particular aspects, the dithiothreitol is present at a final concentration of about 0.05 to about 5 mM. In specific aspects, the dithiothreitol is present at a final concentration of about 0.52 mM. In some aspects, the fetal bovine serum has been heat inactivated prior to addition. In certain aspects, the fetal bovine serum is present at a final concentration of between about 2% and about 40%. In specific aspects, the fetal bovine serum is present at a final concentration of about 20%. In a specific aspect, the culture medium comprises CMRL 1066 at a final dilution of 0.8×, sodium pyruvate at a final concentration of 0.73 mM, Resazurin at a final concentration of about 0.001%, MOPS pH7.5 at a final concentration of about 20 mM, $NaHCO3$ at a final concentration of about 19.2 mM. L-glutamine at a final concentration of about 2 mM, D-glucose at a final concentration of about 17.6 mM, D mannitol at a final concentration of about 0.88 mM, L-histidine at a final concentration of about 0.52 mM, DL-dithiothreitol at a final concentration of about 0.52 mM, and heat inactivated fetal bovine serum at a final concentration of about 20%.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: Cumulative generations during in vitro culture of *T. pallidum* subsp. *pallidum* Nichols in Experiment 1. Increases in the primary cultures occurred only within the first 12 days. The number of generations in low inoculum cultures accumulated more rapidly than in the 500 µl inoculum cultures until the latter were discontinued on day 116.

FIGS. 3A-B. Multiplication and genome replication of *T. pallidum* Nichols in Sf1Ep co-cultures and axenic cultures. Fold increases are shown in parentheses. The inoculum for this experiment was from frozen stocks of *T. pallidum* Nichols extracted from infected rabbit testicular tissue. A) The number of *T. pallidum* per culture increased only ~2-fold in axenic cultures, but over 55-fold for co-cultures with Sf1Ep cells. Genome equivalent increases were similar to cell number increases for the Sf1Ep co-cultures, but were somewhat higher than cell number increases for the axenic cultures. B) Genome equivalents per cell remained stable for the exponentially growing co-cultures, but increased for the axenic cultures.

FIGS. 6A-C. Appearance of in vitro cultured *T. pallidum* subsp. *pallidum* Nichols by darkfield light microscopy. This specimen was from a 200-day culture from Experiment 1. A) Four organisms with typical morphology, showing regions with planar, 'flat wave' morphology (arrowheads). B) Example of the inherent flexibility of *T. pallidum*. C) Ring-shaped organism in which the two ends are joined. All of these forms are also commonly seen in *T. pallidum* freshly extracted from rabbit tissue.

FIGS. 7A-F. Structure of *T. pallidum* subsp. *pallidum* Nichols following 54 days of in vitro culture, as determined by cryo-electron microscopy. (A, D) Two *T. pallidum* cells were imaged at low magnification (1 μm bar). (B, C and E, F) Highlighted areas in (A) and (D) were imaged at high magnification (200 nm bar). B) Intact region in the middle of the cell, showing the binding of small (~10 nm) particles or vesicles to the outer membrane surface. C) Region of the cell in A) in which the outer membrane has been stripped off. Note the lack of bound particles. E) End of the cell in D), showing the conical tip structure and a prominent membrane bleb, both typical of *T. pallidum* structure. F) Intact region in middle of cell. The outlines of periplasmic flagella are clearly visible in this and other panels.

FIGS. 8A-B. Effect of medium volume on *T. pallidum* multiplication in the Sf1Ep co-culture system. Equal quantities of *T. pallidum* Nichols were inoculated into triplicate 9 cm$^2$ Sf1Ep cell co-cultures containing 2, 3, or 4 ml of TpCM-2. The cultures were harvested and evaluated for *T. pallidum* fold increase and motility on day 7. A) Increased culture yield with larger medium volumes. B) High retention of motility in all cultures.

FIGS. 9A-C. Pilot experiment showing continued multiplication of *T. pallidum* subsp. *pallidum* Nichols in subcultures during co-incubation with Sf1Ep cells in TpCM-2 medium. Primary cultures were inoculated with a frozen preparation of rabbit-propagated *T. pallidum*. Cultures were trypsinized on days 8, 16, 28, and 36 for *T. pallidum* concentration and motility determinations. One set of subcultures were performed sequentially on days 8, 16, and 28; subcultures were done on days 16 and 28 in the second set. Cumulative fold increases of 978 and 1105 were observed in the two subculture series. A) *T. pallidum* per culture. B) Percent motility. C) Cumulative fold increase.

FIGS. 10A-C. In vitro culture of *T. pallidum* subsp. *pallidum* Nichols (Exp. 2). Parameters are as described in FIG. 1. A) Number of *T. pallidum* per culture. B) Percent motility. C) Average generation time.

FIGS. 11A-B. Replication of the experiment in FIG. 4, showing the effects of Sf1Ep co-culture and axenic culture on *T. pallidum* cell numbers and genome equivalents during in vitro incubation.

FIGS. 12A-C. Successful revival and culture of *T. pallidum* subsp. *pallidum* Nichols from a frozen stock of in vitro cultured organisms. A sample from a day-54 culture from Exp. 1 was supplemented with 15% (v/v) glycerol and frozen at −80° C. The sample was thawed 25 days later and used to inoculate a new set of Sf1Ep cultures. Thawed *T. pallidum* was treated as a primary culture (without subculture) or was subcultured at 6-7 day intervals (with subculture). On day 35, the medium volume was changed from 2 ml to 4 ml. Separate cultures inoculated with frozen, rabbit-propagated *T. pallidum* were included as controls. A) *T. pallidum* per culture. B) Percent motility. C) Average generation time per culture period.

FIGS. 13A-C. Long-term in vitro culture of *T. pallidum* subsp. *pallidum* UW231B (Experiment 4). Sf1Ep cultures were inoculated with frozen, rabbit-derived UW231B. The cultures were either incubated without subculture but with partial medium replacement every 6-7 days (primary cultures), or were subcultured at 6-7 day intervals. A) Number of *T. pallidum* per culture. B) Percent motility. C) Average generation time.

FIGS. 14A-C. Long-term in vitro culture of *T. pallidum* subsp. *pallidum* UW249B (Experiment 5). Conditions are as described for UW231B in FIG. 12. The experiment was discontinued at day 40 due to fungal contamination in the subsequent subculture. A) Number of *T. pallidum* per culture. B) Percent motility. C) Average generation time.

DESCRIPTION OF ILLUSTRATIVE EMBODIMENTS

Figure 1:
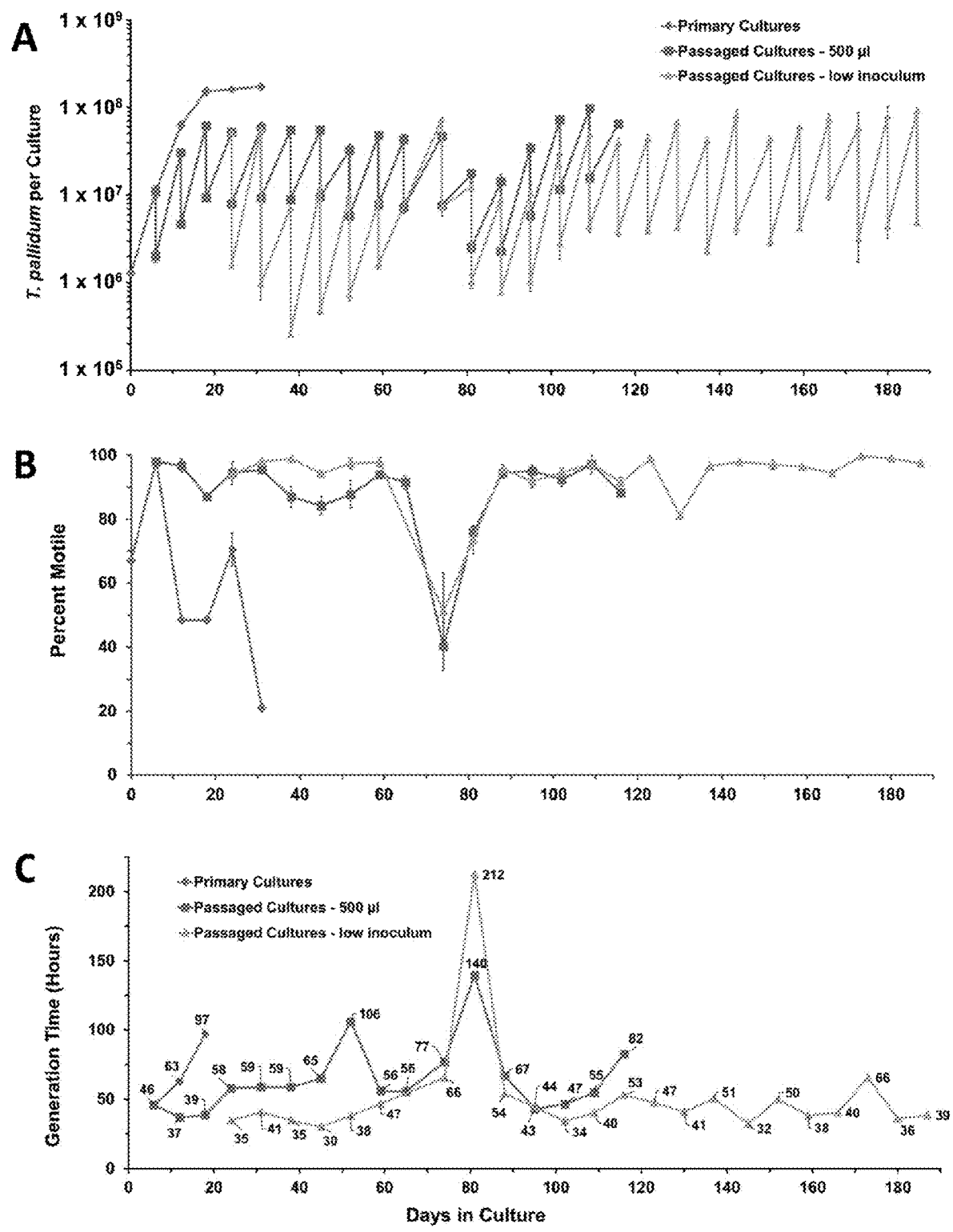
FIGS. 1A-C: Long-term cultivation of *T. pallidum* subsp. *pallidum* Nichols in a tissue culture system (Experiment 1). Primary cultures represent the results obtained without subculture. The 500 µl passages used transfer of that volume for each subculture, whereas low inoculum passages used smaller volumes (100 µl to 250 µl). Each timepoint represents the mean+S.E. of three biologic replicates. A) In this 'sawtooth' plot, the number of *T. pallidum* per culture upon harvest and the number inoculated in the next subculture are shown for each time point. B) Percent motility provides a measure of viability. C) Average generation time, representing the time in hours divided by $log_2$ (fold increase) for each time point.

Investigation of *Treponema pallidum* subsp. *pallidum*, the spiral-shaped bacterium that causes syphilis, has been hindered by an inability to culture the organism continuously in vitro despite more than a century of effort. In some aspects, the instant disclosure addresses these issues by providing methods for long-term logarithmic multiplication of *T. pallidum* through periodic subculture and feeding with a modified medium in microaerobic rabbit epithelial cell co-incubation system. For instance, in specific examples, subculture occurs every ~6-7 days and periodic feeding is maintained using a modified medium (e.g., TpCM-2) in the described microaerobic, rabbit epithelial cell co-incubation system. Using such a system, cultures have maintained continuous growth for over six months with full retention of viability as measured by motility and rabbit infectivity. This system has been applied successfully to the well-studied Nichols strain of *T. pallidum*, as well as two more recent syphilis isolates, UW231B and UW249B. Light microscopy and cryoelectron microscopy showed that in vitro cultured *T. pallidum* retain wild-type morphology. Importantly, culture systems and method of the embodiments can facilitate study of the physiologic, genetic, pathologic, immunologic, and antimicrobial susceptibility properties of *T. pallidum* subsp. *pallidum* and related pathogenic *Treponema* species and subspecies.

I. CULTURE SYSTEMS OF THE EMBODIMENTS

Studies below describe the first consistent long-term in vitro cultivation of *T. pallidum*, such as, *T. pallidum* subsp.

*pallidum*. The successful culture of syphilis isolates UW231B and UW249B as well as the long-established Nichols strain indicates that the cultivation procedure is applicable to other syphilis isolates or other *Treponema* subspecies or species. For example, the methods may be applied to *T. pallidum* subsp. *pertenue, T. pallidum* subsp. *endemicum, T. carateum*, and *T. paraluiscuniculi*, given the close relatedness of these organisms.

In some aspects, by combining Sf1Ep cells, oxygen gradients (e.g., formed in Leighton tubes) to establish microaerobic conditions, and select lots of medium components such as FBS with Eagle's MEM and DTT to decrease the presence of reactive oxygen species, consistent in vitro multiplication was achieved and reproduced over multiple experiments. In certain aspects, the combination of the modified medium TpCM-2 and the maintenance of near-homeostatic conditions through regular subculture and partial medium replacement as needed allows for the long-term culture of *T. pallidum*. TpCM-2 differs from TpCM by substitution of Eagle's MEM with CMRL 1066 as the basal medium, and the omission of some of the TpCM additives (Table 1). In comparison to MEM, CMRL contains additional nutrients, including nucleic acid bases, nucleosides, cocarboxylase, Coenzyme A, flavin adenine dinucleotide, NAD, NADP, Na acetate, Na glucouronate, and the fatty acid mixture Tween 80; some of the shared components are also present at different concentrations.

TABLE 1

Exemplary *T. pallidum* Cultivation Medium (TpCM-2)

| Component | Amount for 50 ml | Final Concentration | Manufacturer/ Catalog No. |
|---|---|---|---|
| 1X CMRL 1066 without L-Glutamine or Phenol Red | 37 ml | 0.8X | US Biological/ C5900-03A |
| Sodium pyruvate | 364 μl | 0.73 mM | Sigma/S8636 |
| 0.1% Resazurin | 50 μl | 0.001% | Sigma/R7017 |
| 1M MOPS, pH 7.5 | 1 ml | 20 mM | Sigma/M3183 |
| NaHCO3 (7.5%) | 1.08 ml | 19.2 mM | Sigma/M8761 |
| 200 mM L-Glutamine | 500 μl | 2 mM | Sigma/G6152 |
| 100X D-glucose (15% in water) | 500 μl | To 17.6 mM | Sigma/G6152 |
| D-Mannitol (10 g/dl) (10% in water) | 80 μl | 0.88 mM | Sigma/M-1902 |
| L-Histidine (5 g/dl) (5% in water) | 80 μl | 0.52 mM | Sigma/H6034 |
| DL-Dithiothreitol | 4 mg | 0.52 mM | Sigma/D9779 |
| Fetal Bovine Serum, Heat Inactivated | 10 ml | 20% | Sigma/F4135 |

In some cases, culture methods of the embodiments involve regular subculture at e.g., 2 to 10-day intervals, such as every 3, 4, 5, 6, 7, 8 9 or 10 days (e.g., 6-7 day intervals). The relatively short time between subcultures, may in some aspects, limit both the depletion of nutrients and/or the development of toxic conditions, e.g. changes in pH and accumulation of toxic byproducts. In some aspects, the subculture interval can be increased when the number of *T. pallidum* in culture is low and partial medium replacement is utilized. For example, in some low inoculum studies the inocula became $\leq 10^6$ per culture. To bolster these cultures, they may be extended up to 15 days with partial medium replacement at 4 to 7 day intervals (e.g. FIG. 1, low inoculum, days 59-74).

The compounds that are present in CMRL 1066 but absent in Eagle's MEM (Table 2) may to contribute to the successful long-term culture of *T. pallidum* utilizing the TpCM2 medium. Utilization of other media of varied formulations that contain one or more of the compounds in Table 2 could support long-term survival and multiplication of *T. pallidum*. There are also a number of compounds that are present in different concentrations in the CMRL 1066 basal medium used in TpCM2, when compared to the concentrations in Eagle's MEM (Table 3). Some compounds are present in higher concentrations in CMRL 1066 medium, whereas others are present in higher concentrations in Eagle's MEM. Thus, the concentrations of these compounds may be altered (for example 0.01-fold, 0.1-fold, 10-fold, and 100-fold concentrations) to support the long-term survival and multiplication of *T. pallidum*. Different concentrations of the compounds in Table 2 can enhance the survival and growth of *T. pallidum*, e.g. result in higher yields per culture or longer survival between transfers under otherwise identical conditions.

TABLE 2

Compounds present in CMRL-1066 and not present in Eagle's MEM.

| Compound | Amount present (g/L) |
|---|---|
| Sodium Acetate, anhydrous | 0.05 |
| L-Cysteine•HCl•H2O | 0.26 |
| Glycine | 0.05 |
| trans-4-Hydroxy-L-Proline | 0.01 |
| L-Ascorbic Acid | 0.05 |
| Cocarboxylase | 0.001 |
| Coenzyme A•Na | 0.0025 |
| 2'-Deoxyadenosine | 0.01 |
| 2'-Deoxyguanosine | 0.01 |
| 2'-Deoxycytidine•HCl | 0.0116 |
| Flavin Adenine Dinucleotide•2Na | 0.000106 |
| 5-Methyldeoxycytidine | 0.0001 |
| β-NAD | 0.007 |
| β-NADP•sodium | 0.001 |
| Nicotinic Acid | 0.000025 |
| PABA | 0.00005 |
| Pyridoxine•HCl | 0.000025 |
| D-Glucuronic Acid•Na | 0.00388 |
| Glutathione | 0.01 |
| Thymidine | 0.01 |
| Tween 80 | 0.005 |
| Uridine-5-Triphosphate•Na | 0.001 |

TABLE 3

Compounds with differences in concentrations between CMRL-1066 and Eagle's MEM.

| Compound | Amount in CMRL (g/L) | Amount in MEM (g/L) | Difference (g/L) |
|---|---|---|---|
| L-Glutamic Acid, Sodium | 0.075 | 0.0147 | 0.0603 |
| L-Proline | 0.04 | 0.0115 | 0.0285 |
| L-Aspartic Acid | 0.03 | 0.0133 | 0.0167 |
| L-Alanine | 0.025 | 0.0089 | 0.0161 |
| L-Serine | 0.025 | 0.0105 | 0.0145 |
| L-Leucine | 0.06 | 0.052 | 0.008 |
| Magnesium Sulfate, anhydrous | 0.09769 | 0.09767 | 2E−05 |
| Riboflavin | 0.00001 | 0.0001 | −0.00009 |
| Choline Chloride | 0.0005 | 0.001 | −0.0005 |
| Niacinamide | 0.000025 | 0.001 | −0.000975 |
| Pyridoxal•HCl | 0.000025 | 0.001 | −0.000975 |
| Folic Acid | 0.00001 | 0.001 | −0.00099 |
| D-Pantothenic Acid•Ca | 0.00001 | 0.001 | −0.00099 |
| Thiamine•HCl | 0.00001 | 0.001 | −0.00099 |
| myo-Inositol | 0.00005 | 0.002 | −0.00195 |
| L-Lysine•HCl | 0.07 | 0.0725 | −0.0025 |
| L-Cystine•2HCl | 0.026 | 0.0313 | −0.0053 |
| L-Phenylalanine | 0.025 | 0.032 | −0.007 |

TABLE 3-continued Compounds with differences in concentrations between CMRL-1066 and Eagle's MEM.

| Compound | Amount in CMRL (g/L) | Amount in MEM (g/L) | Difference (g/L) |
|---|---|---|---|
| L-Tyrosine | 0.04 | 0.0519 | −0.0119 |
| L-Asparagine•H2O | 0 | 0.015 | −0.015 |
| L-Threonine | 0.03 | 0.048 | −0.018 |
| L-Valine | 0.025 | 0.046 | −0.021 |
| L-Histidine•HCl•H2O | 0.02 | 0.042 | −0.022 |
| L-Isoleucine | 0.02 | 0.052 | −0.032 |
| L-Arginine | 0.05787 | 0.126 | −0.06813 |

In some aspects, an increase in the volume of medium can result in a proportionately improved yield and retention of motility when a high inoculum was used (FIG. 8). Thus, methods of the embodiments can comprise media addition in addition to, or to substitute for subculture steps.

Robust growth of *T. pallidum* in this system was found in the presence of Sf1Ep cells, with little multiplication occurring in parallel axenic cultures (FIG. 3, FIG. 11). It is of interest that the number of genome equivalents per cell increased dramatically in axenic cultures, whereas this value remains relatively constant at ~3 genome equivalents per cell in parallel cultures with Sf1Ep cells. The direct interaction through adherence between Sf1Ep cells and *T. pallidum* is by be important for promotion of treponemal multiplication. In some studies, the separation of *T. pallidum* from the cell monolayer in TransWell chambers can be detrimental to growth. Without being bound by any particular hypothesis, in some cases, *T. pallidum* may directly acquire certain nutrients, such as lipids, through direct interaction with host cells as these organisms contain the genes required for fatty acid synthesis. The bound particles or vesicles observed by cryo-electron microscopy (FIG. 7) may represent a means of nutrient acquisition. It is also possible that the co-culture cells, such as Sf1Ep cells, provide one or more protective activities, e.g. the scavenging of reactive oxygen species. In some cases, the capability of cells to support *T. pallidum* multiplication may be enhanced by a slow growth rate and/or low metabolic activity. For example, Sf1Ep cell cultures can survive quite well for two weeks, with little change in medium parameters such as pH.

In summary, the culture system described herein will facilitate the characterization of *Treponema* species such as *T. pallidum* subspecies, *T. carateum*, T. paraluiscuniculi. *T. pallidum* subsp. *pertenue* and subsp. *endemicum*. Likewise, the instant methods and systems may be applied to rabbit and hare pathogen *T. paraluiscuniculi*, which may provide new insights into the evolution of host specificity among *Treponema* species. The disclosed methods, will enable isolation of *T. pallidum* and other pathogenic *Treponema* directly from tissues or body fluids using the in vitro culture system. This approach also may also permit the culture of the pinta organism *T. carateum*. Such in vitro cultured organisms could also be used in in vitro host-pathogen interaction and immunologic studies, as well as in vaccine and drug development.

II. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Ethics Statement.

All procedures involving rabbits were reviewed and approved by the Animal Welfare Committee of the University of Texas Health Science Center at Houston.

Tissue Culture.

All reagents were purchased from Sigma-Aldrich unless otherwise indicated. Sf1Ep (NBL-11) cells (ATCC® CCL68™) were obtained from the American Type Culture Collection, Rockville, Md. Stocks of Sf1EP cells were between passage 19 and 40 and were maintained in Sf1Ep medium consisting of Eagle's MEM with non-essential amino acids, L-glutamine, sodium pyruvate, and 10% heat-inactivated FBS (46) at 37° C. in air with 5% $CO_2$. Low passage Sf1Ep grow slowly and were subcultured 1:5 every two to three weeks. High passage cells grow more rapidly and were subcultured 1:20 every week. Cells were fed weekly by replacement of one half of the medium volume.

Bacteria.

*Treponema pallidum* subspecies *pallidum* Nichols, initially isolated from the cerebrospinal fluid of a neurosyphilis patient in Baltimore, Md., U.S.A. in 1912 (Nichols and Hough, 1913), was obtained from J. N. Miller at the UCLA Geffen School of Medicine. The UW231B and UW249B strains were isolated in 2004 from the blood of untreated syphilis patients in Seattle, Wash., U.S.A. and were the kind gift of L. C. Tantalo, S. K. Sahi, and C. M. Marra (University of Washington School of Medicine). *T. pallidum* strains were maintained by intratesticular passage in male New Zealand white rabbits (3-4 kg) that were housed at 16-18° C. and provided antibiotic free food and water. Rabbits were inoculated with $2 \times 10^7$ to $5 \times 10^7$ organisms from frozen stocks per testis. Animals infected with the Nichols strain were euthanized at the time of peak orchitis (10 to 12 d). Infection with the UW strains was monitored by RPR reactivity, and the animals were euthanized when a positive test result was obtained (20 to 40 d for UW231B, 26 d for UW249B). Testes were removed aseptically and *T. pallidum* were extracted from minced testes by gentle stirring in 10 ml of filter-sterilized phosphate buffered saline (PBS; 0.154M NaCl, 0.01M $NaHPO_4$, pH 7.4) with 50% heat inactivated rabbit serum and 1 mM DTT for 10 minutes. Rabbit cells were removed by centrifugation at 100×g for 7 minutes. The *T. pallidum* suspension was supplemented with 15% (v/v) sterile glycerol and stored in 1 ml aliquots at −80° C. In vitro cultured *T. pallidum* were frozen in TpCM-2 medium supplemented with 15% glycerol.

*T. pallidum* Cultivation Medium.

TpCM-2 was prepared as indicated in Table 1 one day prior to use. All solutions were made in cell culture grade water (Sigma W3500) and filter sterilized.

Fetal bovine serum lots were pre-screened for their ability to support *T. pallidum* replication and heat inactivated at 56° C. for 30 minutes. The pH of the medium was adjusted to 7.5 and then filter sterilized with 0.22 µm polyethersulfone filters (Merck Millipore). The medium was then pre-equilibrated in a BBL™ GasPak™ jar in which a vacuum was drawn five times (house vacuum, ~12-18 um Hg) and the jar was refilled with 5% $CO_2$:95% $N_2$ four times and a final time with 1.5% $O_2$:5% $CO_2$:93.5% $N_2$. The medium was then incubated overnight in a tri-gas incubator (ThermoFisher Forma Model 3130) maintained at 34° C. and 1.5% $O_2$:5% $CO_2$:93.5% $N_2$ (hereafter referred to as the low oxygen incubator). All subsequent steps in the incubation of *T. pallidum* cultures were carried out under these conditions.

In Vitro Cultivation of *T. pallidum*.

One to two days prior to each culture initiation or passage, Sf1Ep cells were trypsinized and seeded in tissue culture-treated 6-well cluster plates (Falcon 353046) at 0.5-1×10$^5$ per well. Due to the long culture period, the use of plates with low evaporation lids is essential. At least three hours prior to the start of an experiment or passage, the medium in the 6-well plates containing Sf1EP cells was removed, and the plates were rinsed with the pre-equilibrated TpCM-2 to remove traces of Sf1Ep medium prior to addition of 2 to 4 ml of the TpCM-2. Plates were then pre-equilibrated in the GasPak jar as described above and then transferred to the low oxygen incubator. All manipulations of cultures were carried out in ambient air with use of a laminar flow hood, with efforts to limit this air exposure to <30 min to limit oxygen exposure.

Cultivation experiments were initiated using frozen aliquots of *T. pallidum* extracted from rabbits. A frozen aliquot was thawed at room temperature and diluted in TpCM-2, such that each 50-100 μl inoculum contained 0.5-1.25×10$^6$ *T. pallidum*. Sf1Ep cultures were briefly removed from the incubator, inoculated with *T. pallidum*, pre-equilibrated, and then returned to the low oxygen incubator.

Subculture Procedure.

After six to seven days of incubation, *T. pallidum* were subcultured as follows. The TpCM-2 medium was removed and reserved. Each well was rinsed with 0.35 ml of trypsin-EDTA (Sigma T4049) which was combined with the reserved medium. An additional 0.35 ml of trypsin-EDTA was added and the plates were incubated at 37° C. for 5 min. The reserved medium, rinse and trypsinized Sf1Ep cells and *T. pallidum* were combined and used to rinse the culture well. An aliquot (ranging from 100-500 μl) of the trypsinized culture was used to inoculate new 6-well Sf1Ep cultures prepared as described above. A minimum of three wells were inoculated per condition.

Quantification of *T. pallidum*.

A minimum of three biological replicates were used for each condition and time point. Trypsinized cultures were quantitated by darkfield microscopy using one of two counting methods. Samples (10 μl) were placed under 22×22 mm coverslips on plain glass slides, and the number of *T. pallidum* in random fields were counted using a 40× objective lens until 10 fields or >50 organisms had been counted. Motility of each organism was also assessed. At least three counts were made for each sample. Using calibration of the field diameter with a stage micrometer, the concentration of organisms per ml was estimated as the average number per field×10$^6$/2.2. Alternatively, cultures were quantitated using Helber counting chambers with Thoma rulings (Hawksley, Lancing, Sussex, UK). Each culture was counted at least twice using this method. Data for ongoing Experiment 2 are provided through May 10, 2018, whereas data from ongoing Experiments 1, 3, and 4 were those collected prior to Apr. 28, 2018.

Quantitative PCR.

Trypsinized cultures were first centrifuged at 500×g to remove Sf1Ep cells, followed by centrifugation of the supernatant at 14,000×g for 10 min to pellet *T. pallidum*. DNA from the pelleted organisms was purified using the DNEasy kit (Qiagen), and 1/50$^{th}$ of the material (2 μl of a total of 100 μl) was used for each of three qPCR reactions per sample. qPCR was performed using iQ™ SYBR green supermix on a C1000 Touch Thermal Cycler (Bio-Rad). The primers used were targeted to the *T. pallidum* DNA Polymerase I gene (polA, TPANIC_0105): 6037TP1 (5'-CAGGATCCGG-CATATGTCC-3' (SEQ ID NO:1)) AND 6037TP2 (5'-AAGTGTGAGCGTCTCATCATTCC-3' (SEQ ID NO:2)). The program consisted of 95° C. for 2 min, followed 39 cycles of 95° C. for 5 s and 60° C. for 30 s. All samples were examined in triplicate technical replicates, and standard curves using purified *T. pallidum* DNA were performed for each plate and had linear regression coefficients of determination ($R^2$) of ≥0.98. No template controls (NTC) and DNA extracted from uninfected Sf1Ep cultures were used as controls to optimize the qPCR assay conditions.

Infectivity Studies.

The infectivity of cultured *T. pallidum* was determined by injecting serial dilutions of the sample intradermally into the shaved backs of rabbits. Dilutions were performed in TpCM-2 and each dilution was inoculated at duplicate sites on each rabbit. The inoculation sites were shaved and examined daily for 45 days for the development of the occurrence of erythema and induration, which together constitute lesion development. Needle aspirates of representative lesions (two per dosage) were examined by darkfield microscopy for the presence of motile treponemes indicating active treponemal infection. Rabbits were provided antibiotic-free food and water, housed at 16-18° C. and shaved daily throughout the course of the experiment. Median infectious dose (ID50) values were determined by the method of Reed and Miinsch (Reed and Munch, 1938).

Light Micrography.

Digital photographs were obtained as described previously (Lin et al., 2015) using a Nikon Eclipse microscope (Nikon, Tokyo, Japan) equipped with Cytoviva X-cite 120 dark-field illumination (Cytoviva, Auburn, Ala., U.S.A.), a CoolSNAP HQ charge-coupled-device (CCD) camera (Photometrics, Tucson, Ariz., U.S.A.), and Nikon NIS-Elements AR3.2 software. Photography was performed with a 100× objective lens with an internal diaphragm (Nikon) under oil immersion.

Cryo-Electron Microscopy.

Bacterial cultures were mixed with 10 nm gold clusters, which were used as fiducial markers, and then deposited onto freshly glow-discharged, holey carbon grids for 1 min. The grids were blotted with filter paper and rapidly frozen in liquid ethane, using a gravity-driven plunger apparatus. The frozen-hydrated specimens were imaged at −170° C. using a Polara G2 electron microscope (FEI Company) equipped with a field emission gun and a direct detection device (Gatan K2 Summit). The microscope was operated at 300 kV with a magnification of ×9,400, resulting in an effective pixel size of 4.5 Å at the specimen level. SerialEM (Mastronarde, 2005) was used to collect low-dose, single-axis tilt series with dose fractionation mode at about 6 μm defocus and a cumulative dose of ~60 e−/Å$^2$ distributed over 35 stacks. Each stack contains ~8 images. Tilt series were collected from −51° to 51° with increment of 3°. Tomoauto (Morado et al., 2016) was used to facilitate data processing which includes drift correction of dose-fractionated data using Motioncorr (Li et al., 2013) and assembly of corrected sums into tilt series, automatic fiducial seed model generation, alignment and contrast transfer function correction of tilt series by IMOD (Kremer et al., 1996), and reconstruction of tilt series into tomograms by Tomo3D (Agulleiro and Fernandez, 2015).

Example 2—Long-Term Culture and Maintenance of *T. pallidum*

Long Term Culture of *T. pallidum*—

*T. pallidum* subsp. *pallidum* Nichols, isolated from the cerebrospinal fluid of a neurosyphilis patient in 1912 (Nichols and Hough, 1913) and the reference strain for this subspecies, was utilized for most experiments, whereas the strains UW231B and UW249B, isolated from the blood of untreated syphilis patients in Seattle, Wash., USA, were used to examine the applicability of the culture method to other syphilis strains. These and all other known to be available *T. pallidum* strains were isolated and propagated by inoculation of rabbits. The in vitro cultures were initiated with frozen preparations of *T. pallidum* previously extracted from infected rabbit testes and stored at −80° C.

In preliminary studies, multiple modifications of the *T. pallidum* Cultivation Medium (TpCM) described by Cox (Cox, 1994) were examined to determine their effects on treponemal survival and growth. The basal medium of TpCM consists of Eagle's Minimal Essential Medium with added nonessential amino acids. It was found that replacement of the Eagle's MEM component with the more complex CMRL 1066 tissue culture medium (Parker, 1961) resulted in increased yields and improved retention of motility of *T. pallidum* during primary culture in vitro. The $CoCl_2$, cocarboxylase, catalase, and bovine superoxide dismutase components of TpCM did not have a measurable effect on *T. pallidum* in vitro in subsequent analysis and thus were omitted from the formulation described herein.

A pilot experiment provided a positive indication that prolonged in vitro multiplication of *T. pallidum* may be possible with TpCM-2 and Sf1Ep cottontail rabbit epithelial cells. In this study, two different series of subcultures were initiated from a primary *T. pallidum* Nichols culture: one with sequential subcultures on days 8, 16, and 28, and the other on days 18 and 26. Significant multiplication occurred in each of the subcultures, except for the last transfer in the day 8, 16, and 28 series (FIG. 9). In addition, motility was retained above 50% until 28 days. Cumulative fold increase (the product of the fold increase values for each subculture) provided a measure of the sustained multiplication under these conditions (FIG. 9C). While the primary culture increase reached a maximum of 57-fold, the two subculture series achieved cumulative fold increases of 978 and 1,105, respectively. Motility in the subcultures was lost by day 36.

It was reasoned that prolonged survival and growth of *T. pallidum* may be obtained by shortening the subculture interval and thus maintaining more homeostatic conditions.

This culture procedure (outlined in Table 4) utilizes co-incubation of *T. pallidum* with Sf1Ep cells in TpCM-2 at 34° C. in a microaerobic atmosphere consisting of 1.5% $O_2$, 5% $CO_2$, balance $N_2$.

TABLE 4

Outline of *T. pallidum* long-term cultivation parameters 6 well cluster dishes (9 $cm^2$/well)
1 × $10^5$ Sf1Ep cells/well
2 to 4 ml TpCM-2 medium
Preincubation of medium and Sf1Ep cells in 1.5% $O_2$, 5% $CO_2$, balance $N_2$
Inoculation with 0.5-1.25 × $10^6$ *T. pallidum* per well, triplicate wells per condition
Incubation for 6-7 days at 34° C. in 1.5% $O_2$, 5% $CO_2$, balance $N_2$
Replacement of 50% of medium after 3-4 days (optional)
Trypsin/EDTA treatment of 'donor' culture
Inoculation of 'recipient' culture with 0.1 ml to 0.5 ml of trypsinized 'donor' culture
Subculture at 6-7 day intervals Under these conditions, ~90% of the treponemes adhered to the surface of the Sf1Ep cells and multiplied by binary fission. *T. pallidum* were dissociated from the Sf1Ep cells by treatment with trypsin and EDTA, and the resulting suspension used for quantitation by darkfield microscopy and the transfer of organisms to fresh subcultures. In some experiments, a portion of the medium was replaced with fresh TpCM-2 at 3-4 days. The typical subculture interval was 6 to 7 days, although this period could be prolonged if the *T. pallidum* concentration was low. Triplicate cultures in 6-well cluster dishes were utilized for each time point with each culture being used to inoculate a separate subculture, thus maintaining three parallel biological replicates. Details regarding the methodologies utilized are described in the Materials and Methods.

Using these conditions, all five of the *T. pallidum* cultivation experiments that were undertaken to date exhibited consistent, long-term multiplication with retention of motility (Table 5).

TABLE 5

Summary of *T. pallidum* subculture experiments.

| Experiment | Status | Strain | Days in culture | Passage number | Cumulative fold increase | Number of generations | Average generation time (h) | Minimum generation time (h)[a] |
|---|---|---|---|---|---|---|---|---|
| 1 | Ongoing | Nichols | 187 | 26 | 1.1 × $10^{30}$ | 100 | 45 | 33 |
| 2 | Ongoing | Nichols | 189 | 27 | 2.4 × $10^{31}$ | 104 | 54 | 33 |
| 3 | Ongoing | Nichols[b] | 119 | 17 | 2.4 × $10^{19}$ | 64 | 44 | 36 |
| 4 | Ongoing | UW231B | 70 | 9 | 2.6 × $10^9$ | 31 | 54 | 44 |
| 5 | Complete | UW249B[c] | 47 | 6 | 6.5 × $10^7$ | 26 | 52 | 46 |

[a]Minimum generation time = average of the 5 lowest subculture generation times (3 for Experiment 5)
[b]Experiment 3 was initiated from frozen stocks of a day 54 culture from Experiment 1. All other experiments were initiated from 693 frozen preparations of rabbit-propagated *T. pallidum*.
[c]Experiment 5 was discontinued on day 47 because of fungal contamination.

The current results of the longest ongoing *T. pallidum* culture experiment (Exp. 1) are depicted in FIG. 1. The number of *T. pallidum* per culture are shown in the 'sawtooth' graph in FIG. 1A, in which the mean number (±S.E.)

of organisms harvested and inoculated in the subcultures are shown for each time point. In this and subsequent experiments, parallel non-passaged ('primary') cultures were included for comparison. During the first three subcultures, a volume of 0.5 ml (labeled '500 µl', from the total trypsinized culture volume of ~2.4 ml) was used. However, it was noted that these cultures hit a maximum number of roughly $5 \times 10^7$ T. pallidum per culture and exhibited some loss of motility. Therefore, beginning on day 24, parallel subcultures were begun that contained a lower inoculum of 0.1 to 0.25 ml ('low inoculum'). The transferred volume was typically 0.25 ml for these cultures but was adjusted to a lower volume if a particularly high T. pallidum concentration was observed during a brief microscopic examination. Note that a given volume of trypsinized culture was used for inoculation rather than adjusting the inoculum to a certain number of bacteria (which would require an accurate microscopic concentration determination) to minimize the transfer time and thus the exposure to atmospheric levels of oxygen. A typical transfer time was 20 to 30 minutes.

In this representative study, the primary cultures multiplied exponentially for the first 12 days, at which time growth slowed and motility decreased (FIG. 1). In contrast, continued multiplication of T. pallidum occurred in each of the subsequent 25 subcultures, indicating that the replicative potential of the treponemes was retained. In addition, motility (as a measure of cellular viability) was generally maintained at a high level, whereas the motility of the primary cultures decreased dramatically on day 12 (FIG. 1B). A decrease in motility did occur in the subcultures on day 74, when the subculture interval was inadvertently extended to 9 days. However, viability recovered during the following two subcultures, indicating the outgrowth of a subset of organisms that had not been irreversibly damaged. The reduction in the percentage of motile organisms correlated with an increase in the average generation time over the 7-day period of the subsequent subculture (FIG. 1C). Thereafter, the growth of T. pallidum recovered to the prior rate. At the time of this writing, this experiment has been ongoing for 187 days, or over 6 months.

The cumulative generations value for the high inoculum cultures (500 µl) lagged behind that obtained with the parallel low inoculum cultures (FIG. 2). Excluding the variant subcultures on days 74 and 80, the average generation time ranged from 37 to 106 h for 0.5 ml inoculum cultures (mean±S.D.=63±18 h), and 30 to 66 h for the low inoculum cultures (41±8 h) for the time points shared by the two subculture series. T test comparison showed that the generation time was significantly lower ($p \leq 0.05$) in the subcultures receiving a lower inoculum, most likely because optimal multiplication was sustained for a longer time due to slower depletion of required nutrients or accumulation of toxic compounds. For this reason, the high inoculum portion of this experiment was discontinued on day 116.

Very similar results were obtained in a replicate experiment (Exp. 2), which is ongoing at 189 days of culture and 27 subcultures (FIG. 10). Multiplication and motility were consistently maintained except for a downturn on days 98-105 for unknown reasons, with a subsequent recovery. Overall, this experiment had a cumulative fold increase of $2.4 \times 10^{31}$ or 104 generations.

Requirement for Mammalian Cells—

Experiments were performed to examine whether TpCM-2 medium alone could support the long-term survival and growth of T. pallidum Nichols in the absence of mammalian cells (i.e. in axenic cultures). Quantitative PCR was also used to determine the number of T. pallidum genome equivalents per culture during the course of these studies. The results of two experiments (FIG. 3 and FIG. 11) were similar and showed that small (2.0- and 2.2-fold) but statistically significant (p values of 0.013 and 0.039) increases in the number of T. pallidum occurred in axenic cultures during the first 6 days of culture. Motility was also maintained at high levels at this time point (99% and 95%). However, the T. pallidum yield was not significantly higher than the inoculum on day 12 of culture, and motility had decreased (43% and 83%). Interestingly, the number of genome equivalents per cell increased dramatically in the axenic T. pallidum population, while remaining relatively stable in the actively multiplying T. pallidum in the Sf1Ep co-cultures. Thus, only modest multiplication occurred in axenic cultures, but this limitation was apparently not due to the lack of genomic replication.

Successful Freezing and Recovery of In Vitro Cultured T. pallidum—

In vitro cultured T. pallidum Nichols from a subculture harvested on day 54 of Exp. 1 were frozen at −80° C. in TpCM-2 with 15% glycerol. The organisms were thawed 25 days later and used to inoculate fresh cultures (Exp. 3). The thawed T. pallidum exhibited only 3.1-fold increase during the first 7-day culture period, but consistently showed a high replication rate thereafter (e.g. a 14.1-fold increase, or 3.8 doublings during the second 7-day period). This culture has been passaged continuously for 119 days (17 subcultures) and has undergone a $2.4 \times 10^{19}$-fold cumulative fold increase or 26 generations (Table 5, FIG. 12). Thus, in vitro-cultured T. pallidum can be successfully frozen and recovered, raising the possibility of continuous in vitro culture of T. pallidum without a need for rabbit inoculation.

Culture of Additional T. pallidum Strains—

To determine whether this in vitro culture technique can be applied to other T. pallidum strains, long-term culture experiments were performed with two recent syphilis isolates, UW231B and UW249B. These strains are members of the so-called SS14 clade of T. pallidum subsp. pallidum that is currently predominant in the United States, Europe, and many other regions (Arora et al., 2016; Nechvatal et al., 2014; Smajs et al., 2012). As with the prior studies with the Nichols strain, cultures were inoculated with frozen preparations of the UW231B and UW249B strains prepared from infected rabbit testes. The in vitro cultures of UW231B and UW249B exhibited long-term multiplication with retention of motility and wild-type morphology (FIG. 12, FIG. 13). The UW231B cultures are ongoing at 70 days of culture with 9 passages, with a cumulative fold increase of $2.6 \times 10^9$ (31 generations) (Table 5). Similar results were obtained with UW249B (FIG. 13, Table 5), but this culture series was discontinued on day 40 due to subsequent fungal contamination.

Consistency of In Vitro Culture—

Figure 4:
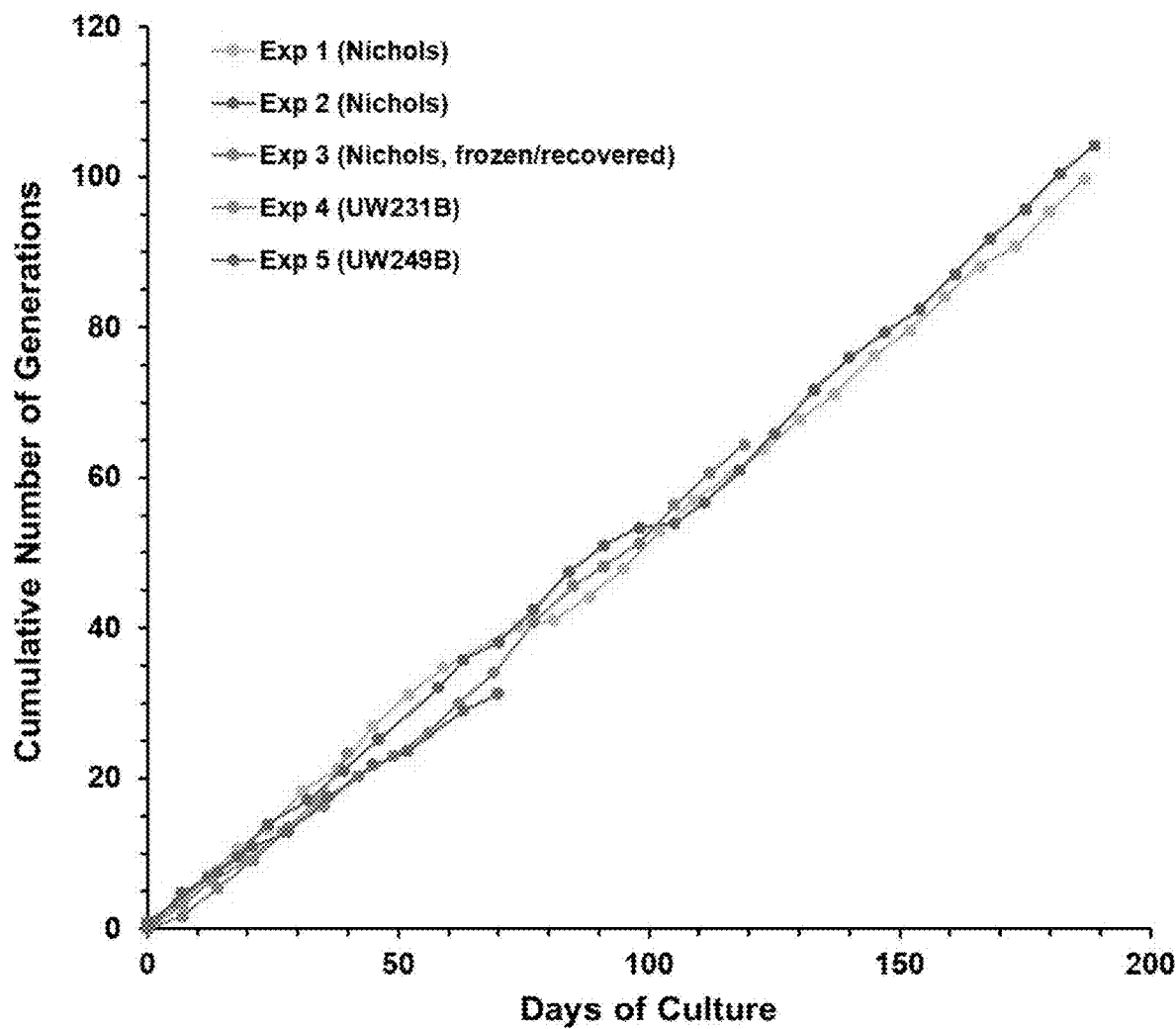
FIG. 4. Consistency of *T. pallidum* multiplication in vitro, as illustrated by cumulative generation values in Experiments 1 through 5.

The growth curves in cumulative generations of the five long-term cultures listed in Table 5 are provided in FIG. 4. The results obtained were remarkably consistent, exhibiting very similar growth rates over time. Additionally, over 20 'side' experiments were inoculated with these long-term cultures and yielded similar results in terms of retention of viability and multiplication.

The doubling time of a bacterium is defined as the time between cell divisions during optimal growth, i.e. the mid-log phase of exponential growth. The doubling time of T. pallidum during rabbit infection is 30-33 h (Magnuson and Eagle, 1948; Cumberland and Turner, 1949). In these in vitro cultures, cell numbers were determined at the beginning and end of 6-7 day subculture intervals, likely including lag, exponential, and early stationary phases. Therefore, only the average generation time for each subculture was calculated, which could be expected to be higher than the exponential doubling time. The average generation times over the entire course of experiments 1 through 5 ranged from 44 to 52 h (Table 5). However, as noted previously, some subcultures had markedly higher generation times (e.g. FIG. 1C). To estimate the minimum generation time, the lowest five subculture generation time values were averaged for each experiment (Table 5); only the lowest 3 generation times were included for Exp. 5, because experiment had only six time points. For the Nichols strain (experiments 1-3), the minimum generation time values were 33.3, 33.3, and 35.6 hours, respectively, whereas somewhat higher values were obtained with strains UW231B (43.8 h) and UW249B (45.8 h). At this point, it is not known if this dissimilarity is due to experimental variation or true biological differences in growth rate. Nevertheless, the results obtained to date indicate that the estimated multiplication rate of *T. pallidum* in vitro is quite similar to that which occurs during experimental rabbit infection.

Infectivity—

Figure 5:
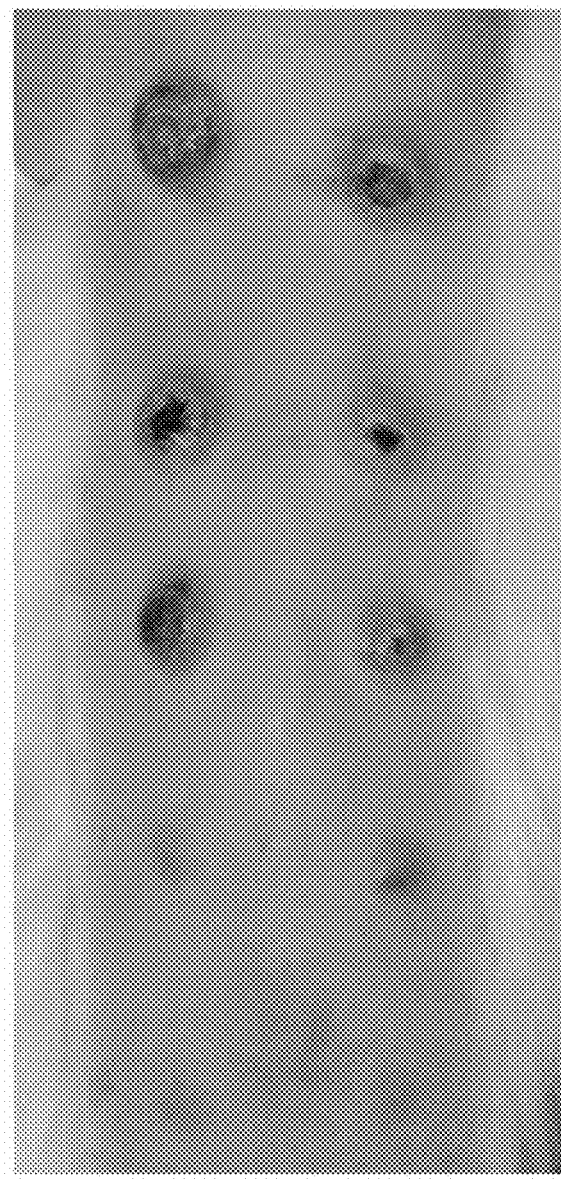
FIG. 5. *T. pallidum* subsp. *pallidum* Nichols cultured in vitro for 116 days are fully infectious in the rabbit intradermal infection model. This photograph of one of the three rabbits in infectivity Experiment A (Table 5) was taken on day 45 post inoculation. Paired sites were inoculated intradermally with the dosages shown. Sites inoculated with higher doses had undergone ulceration, as is typical of intradermal infections in rabbits.

To determine whether *T. pallidum* remained infectious during in vitro culture, two experiments (A and B) were performed in which serial dilutions of *T. pallidum* Nichols from 45- and 116-day in vitro cultures were inoculated intradermally into the shaved backs of rabbits, and the injection sites were observed daily for the development of lesions. Under these conditions, the time of lesion development is inversely proportional to the number of infectious organisms injected, i.e. higher dosages produce lesions more rapidly. The results demonstrate that the in vitro cultured *T. pallidum* remained fully infectious, with dilutions calculated to contain as few as one organism yielding lesions (FIG. 5, Table 6).

TABLE 6

Retention of infectivity by in vitro cultured *T. pallidum* Nichols.

| T. pallidum dosage per Site | Lesions/Sites Inoculated | Day of Lesion Development | Average |
|---|---|---|---|
| Experiment A: Inoculum = 45-day culture | | | |
| 460,000 | 4/4 | 7, 7, 7, 7 | 7 |
| 100,000 | 4/4 | 8, 8, 8, 8 | 8 |
| 10,000 | 4/4 | 9, 11, 11, 11 | 10.5 |
| 100 | 4/4 | 18, 19, 20 | 19 |
| 10 | 4/4 | 21, 26 | 23.5 |
| Experiment B: Inoculum = 116-day culture | | | |
| 10,000 | 6/6 | 11, 11, 11, 11, 11, 12 | 11.2 |
| 1,000 | 6/6 | 11, 11, 11, 11, 11, 12 | 11.2 |
| 100 | 6/6 | 14, 16, 16, 17, 17, 18 | 16.3 |
| 10 | 6/6 | 23, 24, 24, 25, 29, 29 | 25.7 |
| 1 | 6/6 | 19, 36, 36 | 30.3 |

In both experiments, sites injected with as few as 100 organisms developed lesions at all sites. In Experiment A (day 45 organisms), 2 of 4 sites inoculated with 10 *T. pallidum* were positive, whereas in Experiment B (day 116 bacteria) all sites injected with 10 organisms were positive and 3 of 6 sites were positive at the one organism injection sites. Thus, the ID50 of in vitro cultured *T. pallidum* was 10 organisms in Experiment A, and 1 organism in Experiment B, and can be considered to be <10 organisms. Needle aspirates from representative lesions at each dosage were consistently positive for motile treponemes by darkfield microscopy. Exceptions were the lesions from the lowest positive dosages in the two experiments, most likely because the immune response against the previously developing lesions limited the concentration of *T. pallidum* and the lesion size at the lower dose sites (FIG. 5). Overall these results demonstrate that *T. pallidum* cultured in vitro in these studies retain their ability to multiply and cause disease in a widely used animal model of syphilitic infection.

Bacterial Ultrastructure—

*T. pallidum* exhibited characteristic morphology and vigorous motility during the course of in vitro culture, as examined by darkfield microscopy (FIG. 6). Helical to flat plane wave structure was observed. Some organisms had circularized to form ring-shaped structures. Tangled clusters of 2 to 10 bacteria were also present. All of these forms are also commonly observed in *T. pallidum* extracted from infected rabbit tissue.

Cryo-electron microscopy (Cryo-EM) was utilized to determine whether in vitro cultured *T. pallidum* retained the characteristic structure of the organism. As shown in FIG. 7, *T. pallidum* Nichols cultured for 52 days in vitro. It also exhibited a structure that was indistinguishable from that of *T. pallidum* extracted from infected rabbit tissue. The outer membrane, periplasmic flagella, peptidoglycan layer, inner membrane, chemotaxis arrays, conical tip organelles and cytoplasmic filaments were all clearly discernable and identical in appearance to those in rabbit-derived specimens. Interestingly, particles ~10 nm in diameter resembling small vesicles appeared to be bound to the outer membrane (FIG. 7). FIG. 7C shows a region of an organism in which the fragile outer membrane has been stripped off, as commonly occurs in *T. pallidum* preparations. That region is devoid of the small particles, indicating that the particles are binding to the outer membrane surface.

Parameters Affecting In Vitro Growth of *T. pallidum*—

It was thought that the availability of nutrients was limiting in the culture, and, therefore, it was examined whether increasing the volume of TpCM-2 in the cultures could increase yield and survival of *T. pallidum*. Increasing the volume of medium in 6 well cultures from 2 ml to 3 or 4 ml resulted in a concomitant increase in the yield per culture and percent motility (FIG. 8). Therefore, subsequent experiments utilized 4 ml of TpCM-2 per culture. Yield per culture could also be increased by enlarging the size of the cultures from the 6 well cluster dish format (9 cm$^2$ surface area) to 75 cm$^2$ tissue culture flasks. The 75 cm$^2$ flasks have a 9.3-fold higher surface area than a well in a 6-well cluster dish. A proportionately increased number of Sf1Ep cells, a higher medium volume (15 ml), and a larger inoculum were used, essentially 'supersizing' the cultures. Yields were increased by roughly 7- to 10-fold in the 75 cm$^2$ cultures in comparison with 6 well culture controls (Table 7).

TABLE 7

Increased *T. pallidum* culture yield in 75 $cm^2$ cultures relative to 9 $cm^2$ 6-well cultures[a]

| Experiment | 6-well medium volume | 6-well yield (motility) | 6-well fold increase | 75 $cm^2$ flask medium volume | 75 $cm^2$ flask yield (motility) | 75 $cm^2$ flask fold increase | Yield ratio[b] |
|---|---|---|---|---|---|---|---|
| 1 | 2 | $4.5 \times 10^7$ (99%) | 12 | 15 | $3.9 \times 10^8$ (97%) | 9 | 8.7 |
| 2 | 4 | $8.6 \times 10^7$ (98%) | 21 | 15 | $8.7 \times 10^7$ (97%) | 23 | 10 |
| 3 | 4 | $6.5 \times 10^7$ (91%) | 14 | 15 | $4.7 \times 10^8$ (97%) | 13 | 7.2 |
| 4 | 4 | $4.2 \times 10^7$ (99%) | 30 | 15 | $3.0 \times 10^8$ (98%) | 24 | 7.3 |
| 5 | 4 | $9.2 \times 10^7$ (97%) | 21 | 15 | $9.5 \times 10^8$ (99%) | 25 | 10.3 |

[a]Cultures were inoculated with in vitro-derived *T. pallidum* Nichols. The number of organisms added to the 75 $cm^2$ flasks was 9.3x more than added to the 6-well cultures, in proportion to the relative surface area of the cultures. Cultures were incubated for 7 days under standard conditions as described in the Materials and Methods.
[b]Yield ratio = (75 $cm^2$ flask yield)/(6-well culture yield)

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agulleiro and Fernandez, Tomo3D 2.0—exploitation of advanced vector extensions (AVX) for 3D reconstruction. J Struct Biol 189:147-52, 2015.

Arora et al., Origin of modern syphilis and emergence of a pandemic *Treponema pallidum* cluster. Nat Microbiol 2:16245, 2016.

Cox, Culture of *Treponema pallidum*. Meth Enzymol 236: 390-405, 1994.

Ehrlich, Beitrage zur experimentellen Pathologie and Chemiotherapie. AkademischeVerlagsgesellschaft, Leipzig, 1909.

Fieldsteel et al., Cultivation of virulent *Treponema pallidum* in tissue culture. Infect Immun 32:908-915, 1981.

Gensini et al., The contributions of Paul Ehrlich to infectious disease. J Infect 54:221-4, 2007.

Giacani and Lukehart, The endemic treponematoses. Clin Microbiol Rev 27:89-115, 2014.

Kast and Kolmerk, Concerning the cultivation of *Spirochaeta pallida. Amer J Syph* 13: 419, 1929.

Kremer et al., Computer visualization of three-dimensional image data using IMOD. J Struct Biol 116:71-6, 1996.

Li et al., Electron counting and beam-induced motion correction enable near-atomic-resolution single-particle cryo-EM. Nat Methods 10:584-90, 2013.

Lin et al., Mutations in the *Borrelia burgdorferi* Flagellar Type III Secretion System Genes fliH and fliI Profoundly Affect Spirochete Flagellar Assembly, Morphology, Motility, Structure, and Cell Division. mBio 6, 2015.

Magnuson and Eagle, The minimal infectious inoculum of *Spirochaeta pallida* (Nichols strain), and a consideration of its rate of multiplication in vivo. Am J Syph 32:1-18, 1948.

Mastronarde, Automated electron microscope tomography using robust prediction of specimen movements. J Struct Biol 152:36-51, 2005.

Metchnikoff and Roux, Etudes expérimentales sur la syphilis. Ann Inst Pasteur 20:785, 1906.

Morado et al., Using Tomoauto: A Protocol for High-throughput Automated Cryo-electron Tomography. J Vis Exp:e53608., 2016

Nechvatal et al., Syphilis-causing strains belong to separate SS14-like or Nichols-like groups as defined by multilocus analysis of 19 *Treponema pallidum* strains. Int J Med Microbiol 304:645-53, 2014.

Nichols and Hough, Demonstration of *Spirochaeta pallida* in the cerebrospinal fluid from a patient with nervous relapse following the use of salvarsan. J Amer Med Assoc 60:108-110, 1913.

Noguchi, Certain alterations in biological properties of spirochaetes through artificial cultivation, *Ann Inst Pasteur* 30:1-4, 1916.

Norris and Edmondson, Factors affecting the multiplication and subculture of *Treponemapallidum* subsp. *pallidum* in a tissue culture system. Infect Immun 53:534-539, 1987.

Norris et al., Biology of *Treponema pallidum*: correlation of functional activities with genome sequence data. J Mol Microbiol Biotechnol 3:37-62, 2001.

Norris et al., The genus *Treponema*. In Dworkin M, Falkow S, Rosenberg E, Schleifer K-H, Stackebrandt E (ed), The prokaryotes: an evolving electronic resource for the microbiological community, 1st ed. Springer Verlag, Inc., New York, 2003.

Parker, Methods of Tissue Culture, 3rd edition ed. Hoeber Medical Division, Harper & Row, New York, 1961.

Reed and Munch, A simple method of estimating fifty percent endpoints. Am J Hygiene 27:493-497, 1938.

Schaudinn and Hoffman, Vorlaufiger bericht über das Vorkommen für Spirochaeten in syphilitischen Krankheitsprodukten und bei Papillomen. Arb Gesundh Amt Berlin 22:528-534, 1905a.

Schaudinn and Hoffmann, Über Spirochaetenbefunde im Lymphdrilsensaft Syphilitischer. DeutMed Wochenschr 31:711-714, 1905b.

Schereschewsky, Züchtung der Spirochaete pallida (Schaudinn). Deut Med Wochenschr 35:835-559, 1909.

Šmajs et al., Genetic diversity in *Treponema pallidum*: implications for pathogenesis, evolution and molecular diagnostics of syphilis and yaws. Infect Genet Evol 12:191-202, 2012.

von Wassermann et al., Eine serodiagnostische Reaktion bei Syphilis. Dtsch Med Wochenschr 32:745-6, 1906.

World Health Organization. 2016. Report on global sexually transmitted infection surveillance 2015. WHO Document Production Services, Geneva.

What is claimed is:

1. A culture medium comprising CMRL 1066 without L-Glutamine or Phenol Red, sodium pyruvate, Resazurin, MOPS, HaHCO$_3$, fetal bovine serum, L-Glutamine, L-Histidine, D-Mannitol, D-Glucose and DL-Dithiothreitol.

2. The culture medium of claim 1, comprising the following agents and amounts:

| Component | Amount for 50 ml | Final Concentration |
| --- | --- | --- |
| 1X CMRL 1066 without L-Glutamine or Phenol Red | 37 ml | 0.8X |
| Sodium pyruvate | 364 µl | 0.73 mM |
| 0.1% Resazurin | 50 µl | 0.001% |
| 1 M MOPS, pH 7.5 | 1 ml | 20 mM |
| NaHCO3 (7.5%) | 1.08 ml | 19.2 mM |
| 200 mM L-Glutamine | 500 µl | 2 mM |
| 100X D-glucose (15% in water) | 500 µl | To 17.6 mM |
| D-Mannitol (10 g/dl) (10% in water) | 80 µl | 0.88 mM |
| L-Histidine (5 g/dl) (5% in water) | 80 µl | 0.52 mM |
| DL-Dithiothreitol | 4 mg | 0.52 mM |
| Fetal Bovine Serum, Heat Inactivated | 10 ml | 20% |

3. The culture medium of claim 1, comprising one or more of Sodium Acetate, L-Cysteine, Glycine, trans-4-Hydroxy-L-Proline, L-Ascorbic Acid, Cocarboxylase, Coenzyme A, 2'-Deoxyadenosine, 2'-Deoxyguanosine, 2'-Deoxycytidine, Flavin Adenine Dinucleotide, 5-Methyldeoxycytidine, β-NAD, β-NADP•sodium, Nicotinic Acid, PABA, Pyridoxine, D-Glucuronic Acid, Glutathione, Thymidine, Tween 80, and/or Uridine-5-Triphosphate.

4. The culture medium of claim 3, comprising one or more of Sodium Acetate, L-Cysteine, Glycine, trans-4-Hydroxy-L-Proline, L-Ascorbic Acid, Cocarboxylase, Coenzyme A, 2'-Deoxyadenosine, 2'-Deoxyguanosine, 2'-Deoxycytidine, Flavin Adenine Dinucleotide, 5-Methyldeoxycytidine, β-NAD, β-NADP•sodium, Nicotinic Acid, PABA, Pyridoxine, D-Glucuronic Acid, Glutathione, Thymidine, Tween 80, and/or Uridine-5-Triphosphate.

5. A culture system comprising a co-culture of a population of *Treponema* species organisms and a population of mammalian epithelial cells, wherein said co-culture is present in microaerobic conditions and in the presence of a medium of claim 1 comprising excess nutrients and wherein the said *Treponema* species organisms are in direct contact with the mammalian epithelial cells.

6. The system of claim 5, wherein the mammalian epithelial cells are rabbit epithelial cells.

7. The system of claim 6, wherein the cells are Sf1Ep cells.

8. The system of claim 5, wherein the mammalian epithelial cells can be grown for at least 5 days in a medium without depleting the nutrients in the medium.

9. The system of claim 8, wherein the mammalian epithelial cells can be grown for at least 6, 7, 8, 9, 10, 11, 12, 13, 14 or 15 days in a medium without depleting the nutrients in the medium.

10. The system of claim 8, wherein the system comprises at least about $10^5$, $10^6$, $10^7$ or $10^8$ mammalian cells.

11. The system of claim 8, wherein the *Treponema* species organisms are present in the co-culture in a proportion of between about 1:1 and 10,000:1 relative to the mammalian epithelial cells.

12. The system of claim 8, wherein the *Treponema* species organisms are present in the co-culture in a proportion of between about 1:1 and 1,000:1; or 1:1 and 100:1; or 10:1 and 100:1 relative to the mammalian epithelial cells.

13. The system of claim 5, wherein the co-culture is an adherent cell culture.

14. The system of claim 5, wherein the *Treponema* species comprises *T. pallidum, T. carateum,* or *T. paraluiscuniculi*.

15. The system of claim 14, wherein the *Treponema* species comprises *T. pallidum* subsp. *pallidum, T. pallidum* subsp. *pertenue* or *T. pallidum* subsp. *endemicum.*

16. The system of claim 15, wherein the *Treponema* species comprise is *T. pallidum* subsp. *Pallidum.*

17. The system of claim 16, wherein the *Treponema* species comprise *T. pallidum*, subsp. Nichols.

18. The system of claim 5, wherein at least 60% of the *Treponema* species are viable, exhibit motility, and/or exhibit infectivity.

19. A method for culturing cells of the genus *Treponema*, comprising maintain a culture system according to claim 5.

* * * * *